United States Patent [19]

Aubard et al.

[11] Patent Number: 5,017,723
[45] Date of Patent: May 21, 1991

[54] SUBSTITUTED ETHYLAMINES, THEIR PREPARATION PROCESS, THEIR USE AS MEDICINE AND THEIR SYNTHESISING AGENTS

[75] Inventors: Gilbert G. Aubard, Palaiseau; Alain P. Calvet, L'Hay-les Roses; Claude J. Gouret; Agnes M. Grouhel, both of Meudon; Henry L. Jacobelli, Paray Vieille Poste; Jean-Louis Junien, Sevres; Xavier B. Pascaud, Paris; Francois J. Roman, Courbevoie; Claude D. Soulard, Antony, all of France; James P. Hudspeth, Newbury Park; Yuan Lin, Monterey Park, both of Calif.

[73] Assignee: Jouveinal S.A., Paris, France

[21] Appl. No.: 484,493

[22] Filed: Feb. 26, 1990

[51] Int. Cl.$^5$ .................. C07C 211/08; C07C 211/21
[52] U.S. Cl. .................................... 564/383; 564/389; 564/392; 562/465; 562/495; 562/585; 560/356; 558/408; 549/74; 549/492; 546/330
[58] Field of Search ............... 564/360, 366, 373, 336, 564/383

[56] References Cited

U.S. PATENT DOCUMENTS 4,282,251  8/1981  Berney ................................ 564/366

FOREIGN PATENT DOCUMENTS 0298703  6/1988  European Pat. Off. .

OTHER PUBLICATIONS

Jemison et al., JCS Perkin 1, 1450-1457.
Mauze et al., Bull. Soc. Chim. Fr. 1973, (5) p. 1837.

Primary Examiner—Glennon H. Hollrah
Assistant Examiner—Shailendra Kumar
Attorney, Agent, or Firm—Cushman, Darby & Cushman

[57] ABSTRACT

Substituted ethylamines of the formula

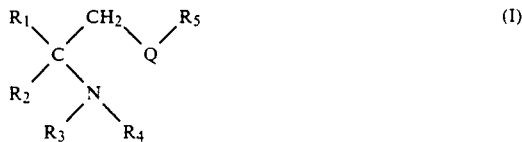

wherein
$R_1$ is phenyl optionally mono-, di- or trisubstituted by halogen, lower alkyl, lower haloalkyl or lower alkoxy, or is an aromatic heterocycle having 5 to 7 chains wherein the heteroatom is nitrogen, oxygen or sulfur,
$R_2$ is lower alkyl,
$R_3$ and $R_4$, each independently, represent hydrogen, lower alkyl or lower alkenyl,
$R_5$ is phenyl optionally mono-, di- or trisubstituted by halogen or lower alkoxy or is an aromatic heterocycle having 5 to 7 chains wherein the heteroatom is nitrogen, oxygen or sulfur and
Q represents a —CH=CH— ethylene group or a 1,2-diyl

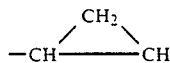

propane group, their acid addition salts and their optically active forms. These substituted ethylamines have psycotropic properties and are useful as medicines.

6 Claims, No Drawings

SUBSTITUTED ETHYLAMINES, THEIR PREPARATION PROCESS, THEIR USE AS MEDICINE AND THEIR SYNTHESISING AGENTS

The invention relates to new substituted ethylamines, their preparation process and their use in the form of therapeutic medicines as well as useful agents for their synthesis.

These ethylamines satisfy the following formula:

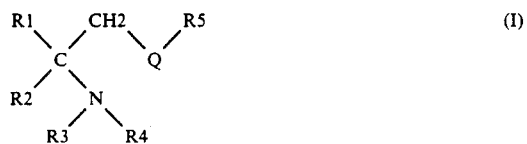

where:
R1 is phenyl possibly mono, di or triisubstituted by halogen atoms, by lower alkyl radicals, lower haloalkyl or lower alkoxy, or is an aromatic heterocycle of 5 to 7 members, in which the hetero atom is nitrogen, oxygen or sulphur.
R2 is lower alkyl
R3 and R4, identical or different, are hydrogen, lower alkyl radicals or lower alkenyl
R5 is phenyl possibly mono, di- or trisubstituted by halogen atoms or by lower alkoxy radicals or is an aromatic heterocycle of 5 to 7 chains in which the hetero atom is nitrogen, oxygen or sulphur.
Q represents an ethylene-1, 2 diyl—CH=CH—group- or a cyclopropane-1,2 diyle

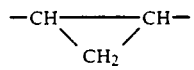

group. The adjective "lower" in the above definitions include the radicals with 1 to 5 carbon atoms in linear or branched chain. Furthermore, the definitions of the R1 to R5 radicals which follow apply particularly to the compounds (I):
R1 is phenyl which can be mono or disubstituted by halogen atoms such as chlorine, lower alkyl radicals such as methyl, lower haloalkyl such as trifluoromethyl or lower alkoxy such as methoxy or is an aromatic heterocycle of 5 chains in which the hetero atom is oxygen as in a furyl radical or sulphur in a thienyl radical or is a pyridyl radical.
R3 and R4 identical or different are hydrogen, lower alkyl like methyl, ethyl, propyl or even lower alkenyl such as allyl
R5 is phenyl possibly mono or trisubstituted by halogen atoms such as chlorine or by lower alkoxy radicals such as methoxy, or is an aromatic heterocycle of 5 chains in which the hetero atom is oxygen as in a furyl radical or sulphur in a thienyl radical.

The invention also includes the added salts of the ethylamines of formula (I) with the mineral or organic acids. Among the salts those obtained by the reaction between the ethylamines and therapeutically acceptable acids are preferred. For example, those prepared with acetic, benzosulphonic, camphosulphonic, citric, sulphonic ethane, fumaric, hydrobromic, hydrochloric, lactic, maleic, malic, sulphonic-methane, mucilic, nitric, pamoic, phosphoric, salicylic, stearic, succinic, sulphuric, tartaric acids.

Formula (I) has one asymmetric carbon atom, which results in the existence of racemic forms and optically active enantiomers for each compound, which are an integral part of the invention. Similarly other possible isomers which can result from the special importance of the R1 to R5 radicals or their association are also part of the invention as are the salified forms of all these compounds as well as their solvated forms.

All the products (I) of the invention are slightly toxic to animals and have important psychotropic properties which justify their use in therapy in the form of medicines.

Nevertheless, the preferred compounds for this application are those in which R1 is phenyl, or is a furyl, thienyle or even a pyridyl radical, R5 is phenyl, furyl or thienyl, R2 is ethyl, R3 and R4 similar or different are hydrogen or methyl and more particularly that they are the following ethylamines (I):
ā-cinnamyl-ā-ethyl-benzylamine, racemic (±/—) levogyre (—), dextrogyre (+) and their salts,
ā-cinnamyl-ā-ethyl-N-methyl-benzylamine racemic (±/—), levogyre (—), dextrogyre (+) and their salts,
ā-cinnamyl-N, N-dimethyl-ā-ethyl-benzylamine racemic (±/—), levogyre (—), dextrogyre (+) and their salts.
ā-cinnamyl-N, N-dimethyl-ā-ethyl-2-thienylmethylamine and their salts,
trans N, N-dimethyl-ā-ethyl-ā-(2-phenyl-1-cyclopropyl methyl)-2-thienylmethylamine and their salts, ā-cinnamyl-N,N-dimethyl-ā-ethyl-2-furylmethylamine and their salts, trans N,N-dimethyl-ā-ethyl-ā-(2-phenyl-1-cyclopropyl methyl)-2-furymethylamine and their salts, Moreover, another group of compounds (1A) of formula (I) had also been singled out in which R1 and R5 are phenyl of which at least one of the two is substituted, Q represents an ethylene-1,2-diyl—CH=CH— and R3 and R4 which are identical or different are the hydrogen or lower alkyl. As R3 and R4 are not both hydrogen, which apart from the psychotropic properties referred to, show an affinity with the opiated receptors "in vitro" and more particularly the mu and kappa receptors. This affinity is translated "in vivo" in the animal by an action on the motivity of the bladder, which means that these products (IA) have a use in treatment of urinary dysfunctions.

The preferred benzylamines of this group are
ā-cinnamyl-N, N-dimethyl-ā-ethyl-p.chlorobenzylamine
ā-cinnamyl-N, N-dimethyl-ā-ethyl-p.methylbenzylamine
ā-(3',4'-dichloro)cinnamyl-N, N-dimethyl-ā-ethyl-p.methylbenzylamine.

The invention also aims at a preparation process of the ethylamines of formula (I), characterised in that it involves mainly and as has been described in diagram 1: to obtain an ethylamine of formula (I.1), agreeing with formula (I), in which R3 and R4 are hydrogen, to hydrolyse an isocyanate of the formula:

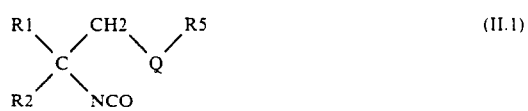

to obtain an ethylamine of formula (I.2), agreeing with formula (I) in which R3 is methyl and R4 is hydrogen,
i) reducing an isocyanate of formula (II.1) by a metallic hydride or,
ii) acylating an ethylamine (I.1) into a N-formyl intermediate compound by formic acid in the presence of carbonyldiimidazole:

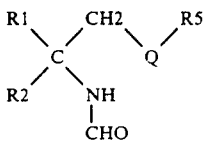

then reducing this intermediate agent by a metallic hydride,
to obtain an ethylamine or formula (I.2), agreeing with formula (I) in which R1 is lower alkyl other than methyl or lower alkanyl and R4 is hydrogen,
i) alkylating an ethylamine of formula (I.1) by means of a Z1R3 halogenide in which R3 is as has been defined above and Z1 is the chlorine, the bromine or the iodine, or
ii) acylating an ethylamine (I.1) by a (R6-CO)n Z2 reagent in which R6 is the carbonated counterpart directly below R3 (R3=—CH2-R6) and the value of n is 1 when Z2 is a halogen like chlorine or bromine or when Z2 is a hydroxyl radical, and n has the value 2 when Z2 represents an oxygen atom to obtain an intermediate carboxamide with the formula

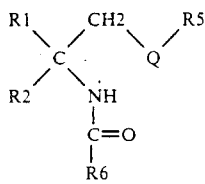 (II.2.1)

then reducing the carboxamid function of the agent by a metallic hydride,
to obtain an ethylamine of the formula (I.3) in which R3 and R4 are identical and are methyl, to dimethylate an ethylamine (I.1) by causing it to react with the formaldehyde and either the formic acid or a reducing metallic or organometallic hydride,
to obtain an ethylamine of the formula (I.3), agreeing with the formula (I) in which R3 is other than hydrogen and R4 is lower alkyl except methyl or its lower alkenyl.
(i) acylating an ethylamine of the formula (I.2) in which R3 is other than hydrogen by means of an acylation agent of the formula R7CO Z5 in which R7 is the immediate counterpart below the R4 (R4=—CH2-R7) and Z5 represents bromine or chlorine to obtain an intermediate carboxamide:

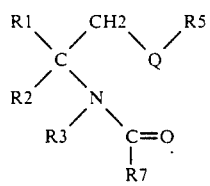 (II.2.2)

then causing a reduction of the carboxamide function by a metallic hydride,
ii) or causing an organomagnesium R2MgZ3 in which R2 is lower alkyl and Z3 a chlorine, bromine or iodine atom to react with an amino-nitrile of formula:

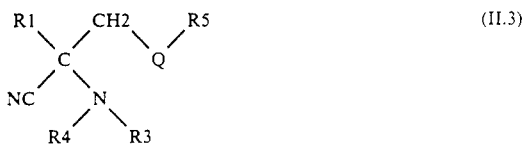 (II.3)

in which R3 and R4, identical or different, are lower alkyl or alkenyl,
to obtain an ethylamine of the formula (I.3) agreeing with the formula (I) in which R3 is lower alkyl or alkenyl and R4 is methyl, N-methylating an ethylamine of the formula (I.2) in which R3 is lower alkyl or alkenyl by the formaldehyde in the presence of a reducing agent such as a metallic or organometallic hydride.

By virtue of the useful intermediate compounds, this invention also relates to the preparation of the ethylamines (I), the compounds of formulae II.1, II.2 and II.3:

 (II.1)

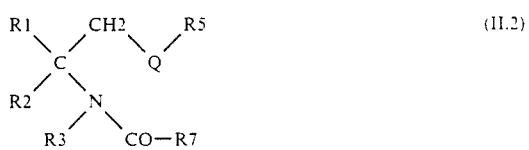 (II.2)

 (II.3)

in which:
the definitions of R1, R2, R5 are identical to those of the formula (I) for the isocyanates (II.1),
the definitions of R1, R2, R3, R5 are identical to those in (I) for the carboxamides (II.2), R7 being hydrogen, a lower alkyl radical, lower alkenyl,
for the nitriles (II.3), R1, R5 are the same as those defined for (I), R3 and R4 equal, except the hydrogen.
The process for preparing the intermediate compounds involves:
alkelating a compound (VIII) R1-CH2-W in which R1 is as has been defined for (I) and W is a nitrile radicle (—CN) or carboxyl (—COOH) using an alkyl halogenide of the formula R2Z6, with R2 as defined in (I) and Z6 being a halogen to obtain an acid of formula (VI)

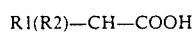

R1(R2)—CH—COOH for W=—CN and to obtain a nitrile of the formula (VII) R1(R2)—CH—CN which is hydrolysed in acid (VI) then alkylating the acid (VI) by a reagent (V) of the formula Z7-CH2-Q-R5, Z7 being a halogen or an alkylsulphonyloxy, and R5 as has been defined in (I) to obtain the acids (III) R1(R2)C(COOH)CH2-Q-R5 aminonitrile (X) by a reagent (V), which has already been described.

DIAGRAM 1:

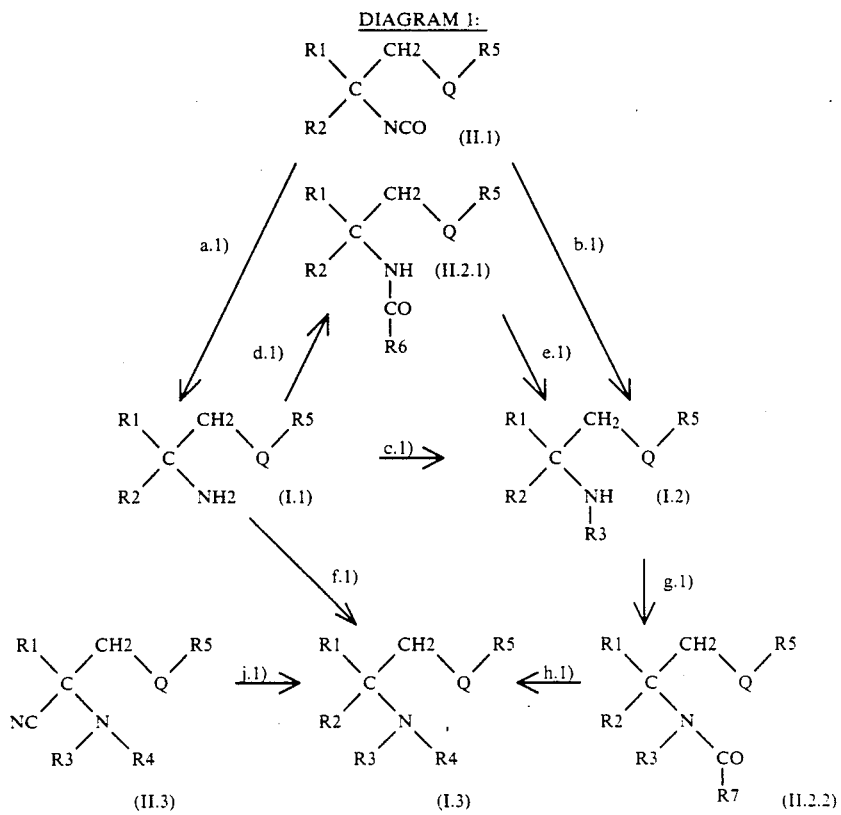

then to prepare the isocyanates (II.1) by the Curtius a.2) reaction starting from these acids, in order to prepare the compound (II.1), to prepare the compounds (II.2), i) in which R3 is hydrogen and which therefore corresponds to the compounds of formula (II.2.1) already defined, accelerating a ethylamine of the invention of formula (I.1) by a reagent (R6-CO)nZ2 already defined, in order to obtain the intermediate carboxomide (II.2) in which R3 is hydrogen and R7 corresponds to R6 of the reagent referred to above, and, ii) in which R3 is alkyl or lower alkenyl and which therefore corresponds to the compounds of formula (II.2.2), to acelate a ethylamine of the formula

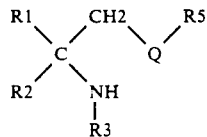

by a halogenide of the formula R7COZ5, in which R7 is hydrogen, lower alkyl or lower alkenyl and Z5 is bromine or chlorine and, to prepare the compounds (II.3) to cause an aldehyde of the formula (XI) R1—CHO to react with an amine of the formula R3-NH-R4 and an alkaline metallic cyanide to obtain an intermediary aminonitrile of the formula (X) R1(CN)CHN(R3)R4 in which R1 is defined as in (I), R3 and R4 also having the definitions of (I), except the hydrogen, then to alkelate the The compounds (I) of the invention are differentiated from the nearest known compounds by their chemical structure and similarly by their application. Hence, L Miginiac and B. Mauzé in the Bull. Soc. Chim. Fr., 1968 (9), p. 3832-44 then Bull. Soc. Chim. Fr., 1973, (5) (Pt. 2), p. 1832-8 report on their research into the reaction of the derived substituted organometallic a-ethylene products with the aldemines of the N-methylamino-1-diphenyl-1,4 butene-3 preparation with the formula C6H5—CH—(NH—CH3)—CH2—CH=CH—C6H5 without giving any application.

Furthermore, RF. W. Jamison et al. in J. Chem. Soc., Perkin Trans. I 1980, p. 1450-7 and 1458-61, during the research into the rearrangements of structures implying intermediate agents of the type "ylide" and catalysed by bases, obtained and described a product f) on page 1451 and on page 1454, which is the N,N-dimethylamino-1(p-nitrophenyl)-1 phenyl-4 butene-3 without giving any application.

These products differ from the ethylamines according to the invention by the nature of the substitution of their amine function and by the fact that the carbon atom linked to this function is only trisubstituted, whereas that of the amines (I) additionally carries an alkyl radical. Furthermore no pharmacological activity that could be applied therapeutically has been reported for these products.

The European patent application no. 0298703 also describes theophene derivatives of the following structure:

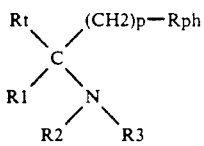

in which in the widest sense,
Rt is a thienyl radical
R1, R2 and R3 represent lower alkyl radicals
RPh is a phenyl radicle, possibly substituted
p has values 1,2 and 3 and in which in the preferred compounds,
R1 is an ethyl radical
R2 and R3 are methyl radicals,
Rph is a phenyl radical,
3,4 dimethyoxyphenyl, 3,4,5-trimethyoxyphenyl or 4 chlorophenyl-p has values 1 or 3.

The compounds have been advertised as slightly toxic and as having a regulatory effect on the motivity of the gastro intestinal tract, characterised by a stimulating effect on a tract of which the activity has slowed down and conversely by an inhibiting effect on a hyperactive tract, such without any objective proof.

Although different in their chemical structure, particularly in the nature of the carbon bonds linking the two aromatic positions and the nature of the substituents of the amino function, the compounds of the European application are also different from the ethylamines (I) of the invention as far as their properties are concerned. In the main no psychotropic type activity has been reported for the compounds in application no. 0298 703, an activity which among other things can be envisaged for the ethylamines (I), which could be used in the treatment of neurophysical complaints.

Independently of the preparation process for the compounds of formula (I), the invention also aims at preparing the intermediate agents (II.1), (II.2) and (II.3).

That of the (II.2) compound, which includes the products of formula (II.2.1) and (II.2.2) has been shown in diagram 1. The preparation process of (II.1) and (II.3) is shown in diagram 2 above and consists of:
preparing the intermediate compounds of formula (II.1) starting from compounds (VIII) of formula R1-CH2-W in which RI is defined as for (I) and W is a nitrile radical (—CN) or also the carboxyl radicle (—COOH) which are subjected to two successive alkeylations in the first instance by a lower alkyl halogenide R2Z6 then by a reagent (V) prepared as shown in diagram 3 and with the formula Z7—CH2—Q—R5 in which R5 and Q are define as (I) and Z7 is a halogen atom such as chlorine or bromine, or even an alkylsulphenyloxy radical.

to prepare the intermediate compounds of formula (II.3) by deoxo cyano-amino substitution in accordance with the Strecker synthesis of aldehydes R1-CHO (XI) and amines R3-NH-R4, compounds in which R1 is a phenyl as described in (I), R3 and R4 are the radicals described in (I), except the hydrogen in the presence of an alkaline cyanide to obtain an aminonitrile (X) which is then alkylated by a reagent (V) to obtain the agent (II.3).

DIAGRAM 2:

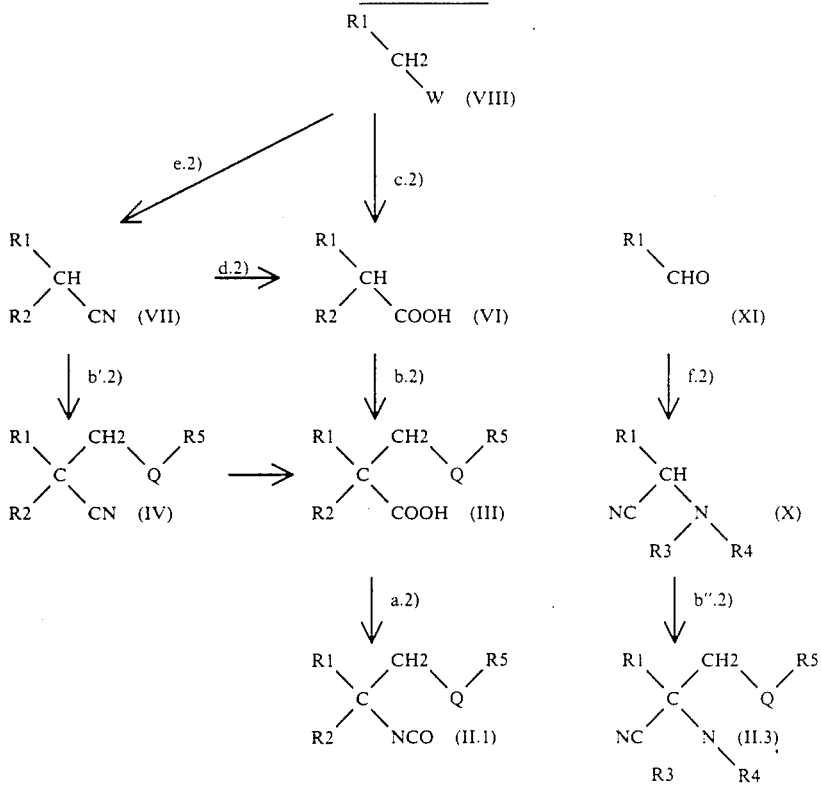

DIAGRAM 3:

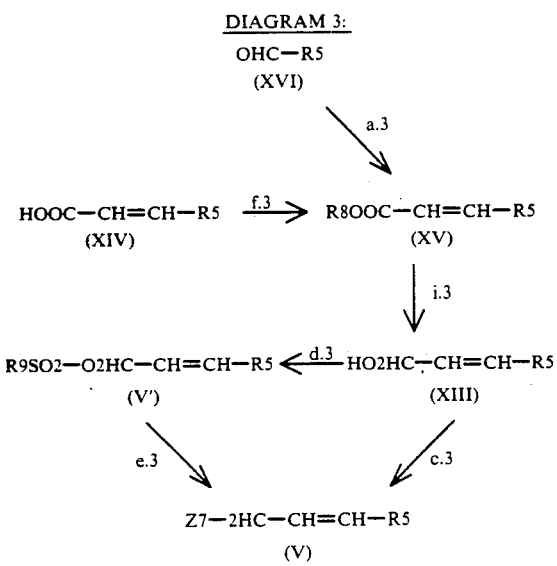

The preparation process of the agents is illustrated in diagrams 2 and 3 and in the detail described below: to obtain what has been shown in diagram 3, a compound (V) in which R5 has the values defined in (I), Q is ethylene-1, 2 diyl—CH=CH— and Z7 is a halogen such as bromine or chlorine, or an alkylsulphonyloxy, the process involves:

i) causing a derived carbonyl product (XVI), R5—CHO, in which R5 has the values defined in (I) to react with a trialkyl phosphonoacetate in the presence of metallic hydride in accordance with the reaction a.3) of Wittig-Horner-Emmons to obtain an ester (XV) in which R8 is a lower alkyl.

As has been described in "Organic Syntheses", Coll. vol. V p. 509, the reaction consists of introducing an inferior trialkyl phosphonoacetate in a metallic hydride suspension in a dipolar solvent at a temperature of between 0° and 20° C. and for a period of between 5 minutes and 1 h 30, then adding the carbonyl derivative (XVI) and heating the reactive environment from 2 h to 8 days then separating the unsaturated ester (XV) obtained. The preferred method for one mole (XVI) consists of using 0.8 to 1.2 moles of triethyl phosphonoacetate and 0.8 to 1.2 moles of sodium hydride and such in an equimolecular ratio. Hence, according to a.3) the triethyl phosphonoacetate is added between 0° and 10° C. to the sodium hydride suspension in the 1,2-dimethoxyethane in approximately 30 minutes then the derived carbonyl product introduced and the mixture stirred at a temperature in the region of 85° C. for a period of 3 to 5 days.

The ester (XV) formed is isolated and purified, then reduced by a metallic or metallo organic hydride in accordance with reaction b.3) in solvents such as ethers, aliphatic or aromatic hydrocarbons.

The metallic elements of these hydrides are aluminium, borium and the alkaline metals are lithium and sodium. Lithium-aluminium hydride (LAH) in an etherised environment in the tetrahydrofurane (THF) or diisobutyl-aluminium hydride (DIBAL-H) (R) in the hexanes, THF or also toluene, which is the preferred solvent for this agent, are used as preferred reducing agents. Hence a sufficient quantity of hydride containing 1.2 to 10 equivalents of active hydrogen is used to reduce 1 mole of ester (XV), with the reaction being carried out at a temperature of between −70° and 40° C. and from 1 to 8 hours. In this way a toluene solution containing 1.0 mole of ester is cooled to a temperature in the neighborhood of −50° C., then a toluene solution containing 2.0 to 2.5 moles of DIBAL-H is introduced for approximately 1 hour while maintaining the same temperature. The reaction is continued for approximately 2 hours at −50° C., then the alcohol (XIII) formed is isolated, purified and employed in the preparation reactions of the derived halogen product (V) by conventional methods described for example in "advanced organic chemistry" J. March, 3rd edition (Wiley) p. 382-383, either in one stage in accordance with reaction c.3) or in two stages in accordance with reactions d.3) and e.3) with reagent (V) in which Z7 is alkylsulphenyloxy.

The reaction c.3) may consist of causing halogen acids or inorganic acid halogenides to react with the alcohol. It is also possible to form an activated intermediate derived alcohol product in the same reaction, unisolated derived product, which leads to the derived product (V), by the "in situ" reaction with an alkaline metallic halogenide such as for example lithium or sodium chloride, bromide, iodide. This reaction consists of causing a trialkyl or triaryl silane halogenide to react with the alcohol (XIII) in an aprotic solvent to form reactivated derivative product which then reacts with the alkaline halogenide; the preferred reagents being the chloro-trialkylsilanes and lithium halogenides. Hence the reaction c.3) consists of introducing 1 mole of alcohol into an acetonitrile solution containing 1.8 to 2.2 moles of lithium bromide and 2.35 to 2.75 moles of chloro trimethylsilane in a nitrogen atmosphere. The reaction is continued from 2 to 24 hours at the reflux of the solvent then the bromated derived product (V) formed is isolated and if necessary purified.

The preparation of the compounds (V) in which Z7 is halogen by means of a sulphonic ester (V') by the successive reactions d.3) and c.3), consists of preparing the sulphonic ester (V) in accordance with d.3) by adding 1 mole of alcohol (XIII) in solution in a halogen solvent such as methylene chloride, 0.8 to 1.2 mole of an acid, mineral or organic acceptor agent, such as preferably triethylamine or 4-dimethylpyridine, then adding 0.8 to 1.2 mol of a halogenide of sulphonic acid at a temperature of between −20° and +30° C. where R9 has been described above and Z4 is a halogen but generally chlorine and after reaction and treatments, to isolate the sulphonic ester and to purify it for example by distillation at reduced pressure, then according to the reaction e.3) to obtain the derived product (V) by substitution of halo-desulphonyloxy, which consists of causing the ester (V) to react with a halogenide in an aprotic solvent in which the halogen is more particularly chlorine or bromine associated with sodium or lithium. The mixture is added to the reflux of the solvent for 4 hours to 7 days to obtain a complete reaction.

In a preferred method 1.4 to 1.8 mol of lithium bromide is added for 1 mol of compound (V') in solution in 2.5 to 3.5 1 of acetone. After 24 hours to 4 days of reaction at the reflux, the bromated derived product (V) obtained is isolated and purified by distillation.

ii) Starting from an unsaturated acid (XIV) to esterify this acid by a R8OH alcohol in which R8 is lower aliphatic alkyl to obtain an ester (XV).

The preferred esterification method f.3) consists of using a Lewis acid such as a boron trihalogenide and more particularly the boron trifluoride - diethyl ether complex as catalyst. Add 0.75 to 1.50 mole of the complex BF3-ether in the conventional way to 1 mol of acid in solution into 1 to 10 l of R80H alcohol. Heat the solution to reflux from 2 to 48 h then treat to obtain the ester (XV) which, possibly purified, is then employed in the reaction b.3) to e.3) already described.

As has already been illustrated in diagram 2, to obtain an agent of the invention with the formula (II.1):

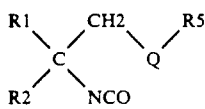
(II.1)

in which R1, R2, R5 and Q are the values denoted by (I)
i) either to monoalkylate an acid R1—CH2—COOH (VIII) acid by an alkyl halogenide R2—Z6 in which Z6 is halogen to obtain an acid (VI): R1—(R2)-CH—COOH, then to carry out a second alkylation with a derivative (V) described and defined previously to obtain the dialkyl acid (III) with the formula:

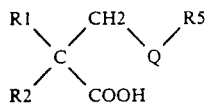
(III)

The alkylation reactions are achieved by known methods as have been described in "Advanced Organic Chemistry" J. March, 3rd edition (Wiley) p. 421, which consists of alkylating the anions of the acids obtained by reaction of strong bases with the acids or their salts.

The strong bases used for this purpose may be metallic or organometallic derivatives of alkaline metals.

Hence, in order to obtain the acids (VI) and when R1 does not contain any halogenised substitute such as chlorine atoms or trifluoromethyl radicals, to use the method described in "Journal of Organic Chemistry" 32, 9, p. 2797-2803, 1967, which consists of preparing the dianion of the acid (VIII) in solution in the tetrahydrofurane by the action of sodium naphthalenate then to cause a halogenide, preferably an iodised derived product to react, in order to obtain the acid (VI) in accordance with reaction c.2) then to achieve the second alkylation of this acid with the derivative VI in accordance with reaction b.2) by a method inspired by that described in "Tetrahedron Lett." 1980, 21 (12) p. 1169-72, which consists mainly of using the lithium diisopropylamide (LDA) to form the dianion reagent.

In a more precise way the first alkylation in accordance with c.2) consists of first of all preparing the sodium naphtalenate in an anhydrous etherised environment like in the THF by the addition of 0.9 to 1 mol of sodium in 0.5 to 1 l of THF for 1 mol of naphthalene in solution then to allow the reaction to develop for 4 to 24 hours and more advantageously from 12 to 18 hours, to add this solution into another solution of THF containing 0.3 to 0.5 mole of acid (VIII) in order to form the dianion reagent by contact lasting 1 to 24 hours at a temperature of between 10° and 50° C. Normally the reaction is completed between 3 and 5 hours at 20° C. and 0.3 to 1.2 mole of halogenous derived product R2-Z6 and more precisely 0.45 to 0.75 mole of derived product where the halogen Z6 is iodine is then introduced. The reaction is complete after stirring between 1 and 48 hours at a temperature of between 10° and 50° C. More favourably the mixture is held at 20°-30° C. for 16 to 20 hours before being treated to obtain the purified compound (VI) expected.

This compound is then used in the second alkylation reaction b.2), which consists of preparing the LDA "in situ" starting from equimolecular quantities of diisopropylamine and butyle lithium then for 1 mole of LDA prepared in this way to add 0.5 to 0.3 mole of acid (VI) in the THF to obtain its dianion. The reagent (V) is then introduced at a temperature of between −10° and +50° C. then the mixture allowed to react for 2 to 48 hours depending on the reactivity of the compounds.

Hence in a preferred manner approximately 0.95 to 1 mole of butyl lithium at −20° C. is added to 1 mol of diisopropylamine in 500 ml of THF then 0.4 to 0.5 mol of acid (VI) in solution to approximately 250 ml of THF. After reacting from 1 to 2 hours at between 20° and 100° C. to form the dianion, the mixture is cooled to 0° C. and 0.4 to 0.5 mole of reagent (V) is added to it.

The reaction is developed for a period of 1 to 2 hours at ambient temperature then the mixture treated to isolate and purify the derived product (III) obtained.

ii) Or to monoalkylate an acetonitrile R1-CH2-CN (VIII) by an alkyl halogenide R2—Z6 previously described to obtain an acetonitrile (VII) of formula R1(R2)-CHCN, in which R1 and R2 are defined as described for (I) in accordance with the reaction d.2). Then according to the hydrolysing reaction d.2) to prepare the acid (VI) which is then treated by the reaction b.2) as previously described to obtain the acid (III). This preparation is preferred when R1 is substituted by halogen atoms, particularly chlorine or by lower haloalkyl radicals such as trifluoromethyl.

In order to achieve this, the method preferably used is described in "Il Farmaco" Ed. Sci. XXV (6) 1970, p. 409-421, which according to the reaction e.2) consists of causing an alkyl halogenide R2—Z6 to react with an acetonitrile (VIII) by a reaction using a catalyst referred to as phase transfer, by introducing one mole of acetonitrile in an aqueous solution of 2.53 mol of this catalyst such as benzyltriethylammonium chloride, which is preferred, then 0.75 to 1 mol of R2—Z6 derivative in which Z6 is bromine or chlorine.

After reacting from 1 to 48 hours and more normally 3 to 5 hours, the mixture is treated and the monoalkyl acetonitrile is purified, generally by distillation at reduced pressure. This nitrile according to the reaction d.2) is hydrolysed, in the first instance by the hydrobromic acid in an ethanol environment then by a concentrated sodium hydroxide solution as has been described in the article referred to.

iii) Or to prepare the dialkyled derived product in accordance with the reaction b'.2) similar to the reaction b.2) already described, which is then hydrolysed to obtain the acid (III).

The alkylation reaction b'.2) consists mainly of only using half the quantity of LDA employed in the reaction b.2), the hydrolysis of the nitrile (IV) obtained by the reaction d.2) already described will then lead to the acid (III).

The intermediate products of the invention of formula (II.1) are prepared in accordance with the Curtius a.2) reaction starting from acids (III) prepared as has just been described in i), ii) and iii).

Various rearranging methods (Hofman, Curtius and Lossen) can be used to prepare isocyanate starting from compounds derived from acid which apply respectively to the reactions referred to, the amides, the acids and hydroxamates.

In a preferred manner the preparation process of the compounds II.1 of the invention uses the Curtius reaction which has been the subject-matter of publications referred to for example in the section "Organic Name Reactions" p. 21 of the "Merck Index" 10th edition. Starting from an acid, it involves successively preparing its chloride then the corresponding azide and finally to obtain the desired isocyanate by thermal decomposition of the latter.

The method advantageously used makes this succession of reactions possible in a single operation and consists of causing the acid (III) to react with sodium azide in the presence of alkyl or aryl dichlorophosphate such as ethyl or phenyl dichlorophosphate and a trialkylamine such as triethylamine or an aromatic amine such as pyridine, which is preferred in an apolar halogenised solvent, then eliminating the solvent and proceeding directly to rearranging the azide formed by the thermal action.

In actual fact, for one mole of acid in solution in 3 to 20 liters of dichloromethane, 1 to 1.75 mol of phenyl dichlorophosphate is added followed by 2 to 3.5 mol of sodium azide and pyridine in equimolecular quantities. The azide is formed at a temperature of between 10° and 40° C. by stirring from 4 to 24 hours depending on the reactivity of the products.

After treatment with water and hydrochloric acid, the dichloromethane is eliminated by distillation or by adding an inert solvent with a boiling point in excess of 100° C. suitable for use as solvent of the thermal decomposition reaction of the acid in isocyanate.

An aromatic solvent like toluene can be used more favourably and the decomposition reaction is carried out at the reflux temperature of this solvent until the end of the gas release which requires a period of between 30 minutes and 8 hours.

The isocyanate (II.1) is obtained after the solvent has evaporated followed by possible purification.
and to obtain the intermediate compounds of the invention with the formula (II.2.1) and (II.2.2) agreeing with the general formula (II.2):

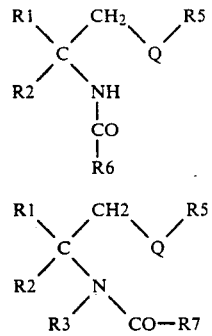

as is shown in diagram 1, where R1, R2, R3, R5 and Q have the values shown in (I) and R6 and R7 are hydrogen, alkyl or lower alkenyl, i) to acylate a compound of the invention (I.1) in which R3 and R4 are hydrogen by the reaction d.1) to obtain a compound (II.2.1) in which R4 is hydrogen and R6 a radical as previously defined.

This acylation is achieved by an agent with the formula (R6CO)nZ2 in which R6, which has already been defined, is the carbonated counterpart directly below the radical R3 (R3=CH2—R6) and in which when n=1, Z2 represents a halogen atom such as chlorine or bromine, except when R6 is hydrogen, or again Z2 represents a hydroxyl and, when n=2, Z2 represents an oxygen atom, ii) or to acylate a benzylamine of the invention (I.2) by the reaction g.1) in which R3 or R4 is hydrogen, the other being alkyl or lower alkenyl to obtain a compound (II.2.2) in which R1, R2, R3 and R4 have been defined previously.

The acylation is then achieved by an agent with the formula R7COZ5 in which R7 is, except for hydrogen, the carbonated counterpart directly below R4 (R4=CH2—R7) and in which Z5 represents a halogen such as chlorine or bromine.

The reactions are carried out in a single phase anhydrous environment in the presence of an organic base or in a 2-phase environment in the presence of an alkaline metal hydroxide when the d.1) and g.1) acylation reactions require the intervention of a reagent in which Z2 or Z5 are a halogen.

The preferred reaction is carried out in a single phase environment in toluene or more favourably dichloromethane, and consists of adding 1.0 to 1.5 mole of amine, which is generally diethylamine to a solution containing 1 mol of derived product to be acylated, then to add a compound R6—COZ2 or R7—COZ5, in which Z2 or Z5 are halogen and such in equimolecular quantity, to the triethylamine. The solution is then kept at a temperature of between 15° and 30° C. from 3 to 48 hours so as to obtain as complete a reaction as possible.

Moreover the method of acylation which consists of causing formic acid to react with the compounds in the presence of 1, 1' carbonildiimidazole in equimolecular relationship with respect to the acid and in an apolar solvent like tetrahydrofurane is preferably used to obtain compounds with the formula (II.2.1) in which R6 is hydrogen.

A 1 to 1.1 mole of each of the reagents is favourably used for 1 mole of product to be acylated, with the reaction being carried out in a homogeneous environment at a temperature of between 15° and 30° C. and lasting from 1 to 48 hours to obtain a complete reaction.

There is a method of preparing a mixed anhydride in situ containing a reagent in which Z2 is hydroxile then to acylate the amine I.1 by this agent, when the acylation reaction consists of causing the compound I.1 to react with this reagent in which Z2 is hydroxile, n=1 and R6 is other than hydrogen.

The reaction is favourably carried out in apolar anhydrous solvents of the ether oxides classification. The tetrahydrofurane is preferred and the anhydrous mixture is in the first instance formed at a temperature of between −40° and 0° C. by adding 1.0 to 1.5 mole of tertiary amine as the N-methylmorpholine then from 0.9 to 1.2 mole of isobutyl chloroformiate to 1 mole of reagent, followed by the addition of 1 mole of the derived product (I.1) to be acylated and the reaction left to develop from 1 to 48 hours at a temperature of between 0° and 60° C. As a rule the result of the reaction is satisfactory at a temperature of between 10° and 25° C. after a period of 10 to 20 hours.

It is also possible in similar conditions to prepare an anhydrous form of the acylation acid agent "in situ" by means of the dicyclohexylcarbodimide then to allow the anhydride formed to react on the aminated derived product (I.1).

Finally, the reaction can be carried out without solvent when the boiling point of the anhydride is below 140° C. when the acylation reagent is an anhydride, namely when n=2 and Z2 is the oxygen, causing the compound I.1 to react extensively and at the reflux temperature of the reagent. However, the preferred method consists of producing the reaction using pyridine as solvent and causing 1 to 5 mole of anhydride to react for 1 mol of compound to be acylated. Usually acceptable results are obtained by using 1.2 to 1.8 mole of anhydride at the reflux of the pyridine for 1 to 3 hours. The derived products (II.2.1) or (II.2.2) obtained are purified by the conventional method if their condition makes it necessary, or employed just as in the reduction reactions which follow to lead to the ethylamines of the invention of formulae (I.2) and (I.3) as is shown in diagram 1.

and to prepare an intermediate amino nitrile product of the invention with structure (II.3)

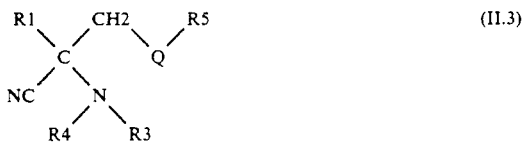

as has been described in diagram 2, in which R1, R5 and Q have the values defined is I, with R3 and R4 also having the values defined in I except the hydrogen, in order to:

i) cause an aldehyde (XI) with the formula R1-CHO to react with a secondary amine R3-NH-R4 in accordance with the reaction f.2) to obtain the amino nitrile (X) with the formula NC(R1)—CH—N (R3)(R4).

This reaction is frequently used to prepare amino acids by the Strecker method. It is used in the synthesis of compounds (X) and consists of causing 1 mole of aldehyde (XI) to react with 0.8 to 3.0 mol of sodium or potassium cyanide and with 0.8 to 3.0 mol of a secondary amine salt with formula R3—NH—R4 in an alcoholic or hydro-alcoholic environment at a temperature of between 5° C. and the reflux temperature of the environment and in a period of between 1 to 24 hours.

The secondary amine salts used are preferably soluble in water like chlorohydrate, bromohydrate, sulphate . . .

The reactive solvent consists of a low molecular weight alcohol and can be mixed in any proportion with water like methanol or ethanol. The respective proportions in the hydroalcoholic environments are between 95 and 10% alcohol for the remainder of 100% being water, this ratio making it possible to obtain a homogeneous reactive environment in a favourable way.

1.0 mol of the aldehyde (XI) in solution in 75 to 200 ml of methanol is added in the conventional way to a solution of 1.1 to 1.3 mol of sodium cyanide and 1.1 to 1.3 mol of secondary amine chlorohydrate in solution in 150 to 400 ml of water. The mixture is stirred for 3 to 5 hours at a temperature between 15° and 30° C. then treated to isolate the amino nitrile (X) which is if necessary purified by distillation.

ii) then to alkylate this compound with a derivative of the formula (V) already described to obtain the agent of the invention (II.3) according to the reaction b".2).
This b".2) reaction is similar to the b'.2) reaction and calls for the same reagents used in identical operating conditions.

Although the processes just described call for known reactions, the preparation of the main products is described in the experimental section of the chapters headed:

"Products used in the synthesis" for the compounds of formula (X), (VI), (V) and (III), "Examples of the products of the invention" described in example 1 for the compounds of formula (II.1) and in example 2 for the compounds of formula (II.3).

By virtue of the processes, the invention is aimed particularly at preparing the racemic or optically active compounds of the invention of formula (I) which may be primary ethylamines (I.1) in which R3 and R4 are hydrogen or secondary benzylamines (I.2) in which R3 and R4 are hydrogen or even tertiary benzylamine (I.3) in which R3 and R4 are other than hydrogen and are defined as in the general formula (I).

The process of preparing ethylamines of the invention (I.1) in which R3 and R4 are hydrogen consists of the hydrolysis of the intermediary isocyanate of the invention (II.1) described previously, in accordance with reaction a.1) of drawing 1.

In a general way, this hydrolysis is catalysed by the acids or the bases preferably inorganic, such as hydrobromic, sulphuric, phosphoric and hydrochloric acids, which is the preferred acid or the alkaline or terreous alkaline metallic hydroxides, with sodium and potassium hydroxides being preferred.

The hydrolysis can be carried out in an aqueous environment or in the presence of a solvent miscible in water and non-reactive to the compounds of the reaction such as ethers like dioxanes and tetrahydrofuranes which is the preferred solvent in the mixture with water.

Hence for 1 mole of derived product (II.1) to be hydrolysed, the reaction is carried out by dissolving the product in 0.5 to 10 liters of THF then adding the water in variable proportions depending on the derived product to be hydrolysed, with the relative composition of the THF-water mixture (v/v) being variable in proportions of between 5-95 and 95-5.

The acid catalyst is added, for example hydrochloric acid in concentrated aqueous solution form in the ratio of 0.2 to 10.0 mol for each mol of compound (II.1) and more generally 0.5 to 5 mol.

The reactive environment is then raised to a temperature of between 50° C. and reflux temperature of the solvents and heated for 2 to 72 hours to obtain a satisfactory quantity of the product.

A heating period of 5 to 24 hours is normally necessary; after which the solvent is eliminated by distillation, the aqueous residue treated to isolate the primary amine (I.1) which is finally purified by distillation, crystallisation or chromatography as has been described in the experimental section of the text.

The preparation process of the ethylamines of the invention (I.2) in which R3 or R4 is hydrogen, with the other radical being defined as stated in the general formula (I): alkyl, lower alkenyl, consists of:

i) reducing an isocyanate (II.1) by the reaction b.1) of drawing 1 described previously, to obtain a compound directly in which R3 or R4 is methyl. A metallic or organo-metallic hydride is to advantage used as reducing agent in suitable condition for the specific reduction of the isocyanate function without acting on the possible ethyl bond Q of the compounds.

To this effect lithium aluminium hydride or aluminium hydride, which is preferred, can be favourably used. The reactions are carried out in solvents inert to the reagents used such as in ethers as for example diethyl ether, 1, 2-dimetoxyethane or tetrahydrofurane (THF) which is preferred.

Also in a preferred manner the aluminium hydride is prepared "in situ" starting from aluminium halogenide and metallic hydrides as has, for example, been explained in "Reduction with complex metal hydrides"—N. G. Gaylord, 1956 Ed. Interscienc e- p. 6 to 8, 51 to 53.

The reduction reaction of 1 mole of isocyanate (I.1) in the THF advantageously consists in the first instance of preparing the aluminium hydride "in situ" by the reaction on 0.75 to 2 moles of aluminium chloride and 2.25 to 6 moles of lithium aluminium hydride, with these reagents being used in a molecular ratio of the order of 1 to 3, then introducing the isocyanate at a temperature of between $-10°$ and $+30°$ C., allowing the reduction reaction to develop for 1-24 hours at the same temperature, then to decompose the reduced complex obtained and isolate the N-methylamine of the formula (I.2) by the conventional methods.

The reductions are most readily carried out at a temperature of between 10° and 20° C. during a period of 2 to 6 hours.

ii) either:
to alkylate a compound of the invention (I.1) by a halogenide Z1-R3 in which R3 has been previously defined and Z1 is chlorine, bromine or iodine according to the reaction d.1) in conditions adapted to favour the monoalkylation of the amine, which is achieved in solvents inert to the reactives such as for example toluene and acetonitrile, and causing 1 mole of amine (I.1) to react with 0.5 to 1.5 mol of halogenide, to obtain an ethylamine in which the R3 is alkyl or lower alkenyl, with R4 being hydrogen.

In a preferred manner 0.80 to 1.2 mol of derived product is used where bromine or iodine is the halogen and an organic or mineral base, is optionally added to favour the reaction which involves heating the reactive environment to a temperature of between 20° and 110° C. and such for a period of 2 to 5 hours, the products being subsequently isolated and purified by the conventional methods, notably by chromatography,
to reduce the carboxamide function of an intermediary compound of the invention (II.2.1) previously described according to the reaction e.1) of drawing 1 to obtain a secondary amine of the invention of formula (I.2).

The reduction is carried out by suitable metallic or organo-metallic hydrides and under conditions adapted to reduce the carboxamide function selectively.

Under these conditions and in a manner similar to the reduction process of the isocyanates according to the reaction b.1) the preferred reducing agent is aluminium hydride which is used in identical operating conditions to those previously described.

The preparation process of the ethylamines of the invention (I.3) in which R3 and R4 are defined as in (I) with the exception of hydrogen and are alkyl or lower alkenyl, involve carrying out a dimethylation of the ethylamines (I.1) of the invention in accordance with the reaction 1.f) which involve causing either formaldehyde in aqueous solution and formic acid to react with a primary amine (I.1) in accordance with the Eschweiler-Clarke reaction either in acetonitrile, formaldehyde in aqueous solution and a reducing agent such as a borium hydride and more advantageously sodium cyanoborohydride in conditions described for example in J. of Med. Chem. 1982, 25, 4, p. 446-51, in order to obtain ethylamines (I.3) in which R3 and R4 are methyl.

The dimethylation according to the Eschweiler-Clarke reaction involves adding 2.0 to 5.0 mole of formaldehyde in aqueous solution at 30-40% by weight per volume to treat 1 mol of amine (I.1) and such at a temperature of between 10° and 50° C., but more favourably between 10° and 30° C. from 30 minutes to 3 hours, then to add the emulsion formed to 2.0 to 10.0 mole of formic acid, either pure or in aqueous solution at a concentration greater than 50% (w/v) then to heat the solution obtained at a temperature of between 50° and 100° C. until the end of the gaseous discharge, which will require 35 minutes to 5 hours depending on the case.

According to the preferred method, an aqueous solution of 2.1 mole of formaldehyde is added to 1 mole of ethylamine (I.1) while energetically homogenising. When the mixture is intimately produced, add 3 moles of pure formic acid to the emulsion. Heat the solution progressively to 100° C. and maintain at this temperature until the end of the gas discharge which will require a period of 1 hour.

The solution is then treated to isolate the ethylamine (I.3) formed which is then purified by the conventional processes notably by chromatography.

ii) and to reduce the carboxamide function of a compound (II.2.2) of preparation previously described to obtain an ethylamine (I.3) in which R3 and R4 are different and are not hydrogen.

The reduction reaction h.1) is carried out with the same reagents and the same method of operation as the reaction e.1) described for the preparation of the ethylamines of the formula (I.2).

iii) and to cause an organo-metallic reagent such as a derived Grignard and organic magnesium of the formula R2 Mg Z3 in which R2 is lower alkyl and Z3 a halogen and more particularly bromine or chlorine to react with an intermediate compound of the invention and in accordance with the reaction i.1) shown in diagram 1, in accordance with a reaction described for example by N. J. Léonard et al., J. Am. Chem. Soc., 1956, 78, p. 1986 and 1957, 79, p. 5279, in order to obtain the benzylamines (I.3) in which R3 and R4 are different and are not hydrogen. This substitution of the nitrile radical of the compound (II.3) by the alkyl radical R2 of the derived organic magnesium compound is carried out in the ethers such as diethylether, methyl-t.butyl ether, the di-isopropyl or dibutyl ethers or also the tetrahydrofurane which is the preferred solvent, and for 1 mol of compound (II.3) involves causing 1.5 to 6 moles of organic material compound derivative to react at a temperature of between 5° and 50° C. and such for a period of 30 minutes to 12 hours.

The preferred method consists of adding 1 mol of compound (II.3) at a temperature of between 10° and 20° C., possibly in solution in THF at 4 to 5 mols of the organic magnesium compound also in solution in the THF. The reaction is continued for a period of 2 to 5 hours at the same temperature then the complex obtained decomposed by the addition of aqueous solution of ammonium chloride. After treatment the ethylamine (I.3) is isolated and purified by the methods already referred to.

The ethylamines of the invention, which are optically active, are prepared by resolving the corresponding racemic forms.

The methods of resolution proposed to achieve this operation are varied and listed in the works of scientific literature such as "Optical resolution procedures for chemical compounds" Vol. 1—Amines and related compounds—Ed. Paul Newman 1981.

The enantiomers are prepared by fractionated crystallisation of their diastereoisomers formed by the reaction of the racemic form with an optically active acid within the framework of the invention.

To this effect numerous acid enantiomers can make these resolutions possible, which are carried out starting from the products of the invention of structure (I.1), (I.2) or (I.3).

Advantageously the process according to the invention consists of forming diastereoisomers of levogyre tartaric acid or dextrogyre tartaric acid in water with the racemic products of formula (I.1).

Normally the precipitate obtained under the conditions used is salt formed by the enantiomer of the rotation ethylamine (I.1) opposed to that of the tartaric acid used.

The products are purified by repeated crystallisation until a stable value of rotational power is obtained.

The methods of operation below illustrate the important intermediary derived products and those of the ethylamines of the invention, without in fact limiting it.

Depending on the reactions carried out, the products are obtained in a satisfactory state of purity, or purified by suitable techniques described in the example, which are generally crystallisation, distillation in vacuum or even chromatography on column. The technique known as "chromatoflash" on a silicon support (make "Merck", product Kieselgel 60, granulometry 230 to 400 mesh) is effectively used in the latter case.

Furthermore, the purity, the identity and the physical-chemical characteristics of the products prepared are recorded and determined by:

their boiling point at the value of the vacuum at the time when they are distilled, their point of fusion determined by the capillary tube method and of which the value indicated is not corrected, chromatography on thin layers (CCM) of silicon (prepared plates when used: "Merck" product reference 60 F 254) using a technique briefly recalled: the products to be analysed are deposited on the plate at the rate of 100 mcg approximately, then eluted by solvents or their mixtures as listed below in an ascendant manner, with the respective proportions being shown in volumes per volume in the list below:

ref. S.A.—hexane 100/ethyl acetate 10
S.B.—hexane 60/ethyl acetate 10
S.C.—hexane 40/ethyl acetate 10
S.D.—hexane 20/ethyl acetate 10
S.E.—hexane 10/ethyl acetate 10
S.F.—dichloromethane 20/hexane 80
S.G.—dichloromethane
S.H.—dichloromethane 90/acetone 10
S.I.—dichloromethane 85/acetone 15
S.J.—dichloromethane 80/acetone 20
S.K.—dichloromethane 98/methanol 2
S.L.—dichloromethane 95/methanol 5
S.M.—dichloromethane 90/methanol 10
S.J.—dichloromethane 85/methanol 15

After development, the chromatograms are examined under ultra violet light of 254 nm wavelength and/or after coloured revelation by pulverising the Dragendorff reagent or the reagent to tolidine. The Rf observed and the references of the elution solvents used are shown in the examples.

The elementary centesimal analysis of which the results are not recorded in a coded manner in conformity with the permissible standard, but are reported to be carried out by representing the dosaged element, the nuclear magnetic resonance of the protons (RMN) is analysed at 60 or 90 MHz, with the products being soluble in deuterochloroform. The aspect of signals, their chemical displacement expressed in ppm with respect to tetramethylsilane used as internal reference are shown. The protons referred to as "interchangeable" after adding the deuterium oxide are also indicated.

The measure of rotatory power is expressed in terms of specific optical rotation of the product ($\bar{a}$) under conditions (concentration, solvent) expressed in the conventional manner. Finally, various reagents or solvents can be expressed in their current abridged form, as among other examples, THF for tetrahydrofurane.

PRODUCTS USED IN THE SYNTHESIS

Products of structure (X)

x.A /$\bar{a}$-dimethylamino phenylacetonitrile
(R1=C6H5; R3=R4 =CH3)

A benzaldehyde solution (0.200 mol) is added to a solution of 11.82 g (0.241 mol) of sodium cyanide and 19.61 g (0.240 mol) of dimethylamine chlorohydrate in 40 ml of water in a reactor in one hour at a temperature of between 30° and 40° C. The mixture is stirred for 4 hours at ambient temperature, then precipitated in 150 ml of icy water and extracted with ether.

The etherised phases are successively washed in water by a 25% of sodium bisulfite solution, then again in water. The residue is purified by distillation after the ether has evaporated. Eb/0.7=74°–79° C.

| Weight = 30.4 g | Rdt = 95% |
|---|---|

The X.b and X.g $\bar{a}$-amino-phenylacetonitrile agents have been prepared by the conventional method and starting from benzaldehydes and suitable secondary amine chlorohydrates.

X.b/$\bar{a}$-(N-allyl, N-methyl) amino-phenylacetonitrile
(R1 = C6H5; R3 = CH3; R4 = CH2=CH—CH2)
Rdt = 78%   Eb/0.1 = 85–90° C.
X.c/$\bar{a}$-dimethylamino-p.chlorophenylacetonitrile
(R1 = p.Cl—C6H4; R3 = AR4 = CH3)
Rdt = 84%   F approximately 50° C. (petroleum ether)
X.d/$\bar{a}$-dimethylamino-3,4-dichlorophenylacetonitrile
(R1 = 3.4(Cl)2—C6H3; R3 = R4 = CH3)
Rdt = 58%   Eb/0.1 = 95–100° C.
X.e/$\bar{a}$-dimethylamino-p.toluylacetonitrile
(R1 = p.CH3—C6H4; R3 = R4 = CH3)
Rdt = 64%   Eb/0.1 = 80–85° C.
X.f/$\bar{a}$-dimethylamino-p.trifluoromethylphenylacetonitrile
(R1 = p.F3C—C6H4; R3 = R4 = CH3)
Rdt = 67%   F approximately 50° C. (petroleum ether)
X.g/$\bar{a}$-dimethylamino-p.methoxyphenylacetonitrile
(R1 = p.CH3O—C6H4; R3 = R4 = CH3)
Rdt = 82%   Eb/0.1 = 95–105° C.
X.h/$\bar{a}$-dimethylamino-$\bar{a}$-[1-(3,4,5-trimethoxyphenyl)] acetonitrile -continued (R1 = 3,4,5(CH3O)3—C6H2; R3 = R4 = CH3)
Rdt = 54%   F = 77° C. (petroleum ether)

X.i/ā-dimethylamino-ā-(2-pyridylyl) acetonitrile (R1 = 2-pyridyl; R3 = R4 = CH3)
Rdt = 67%   Eb/0.5 = 98-110° C.

X.j/ā-dimethylamino-ā-(2-furyl) acetonitrile (R1 = 2-furyl; R3 = R4 = CH3)
Rdt = 58%   Eb/0.1 = 55-75° C.

X.k/ā-dimethylamino-ā-(2-thienyl) acetonitrile (R1 = 2-thienyl; R3 = R4 = CH3)
Rdt = 84%   Eb/0.05 = 75-85° C.

X.l/ā-dimethylamino-ā-(3-thienyl) acetonitrile (R1 = 3-thienyl; R3 = R4 = CH3)
Rdt = 72%   Eb/1.5 = 86° C.

Products of structure (VI) and (VII)

VI.a/2-p.methoxyphenyl butanoic acid
(R1 = p.CH3O—C6H4; R2 = C2H5)

29.4 g (0.23 mol) of naphthalene in 200 ml of THF is introduced into a reactor protected from humidity and in a nitrogen atmosphere. 5.5 g (0.23 mol) of sodium is added to this solution in pieces previously degreased by toluene. A greenish solution is obtained which is continuously stirred overnight.

In addition, 16.6 g (0.10 mol) of p.methoxyphenylacetic acid is dissolved in 200 ml of THF in another reactor. The sodium naphthalanate solution previously prepared is introduced while stirring, the mixture is kept at ambient temperature for 4 hours then approximately 24.3 g (0.15 mol) of ethyl iodide is added in one hour.

After stirring overnight, the suspension is precipitated in 150 ml of sodium carbonate solution at 10% w/v. The aqueous phase is extracted in ether, the organic phases collected and washed by a N HCl solution then by a saturated NaCl solution.

The ether is evaporated, the residue crystallised in 150 ml of petroleum ether.

Weight = 16.1 g   Rdt = 83%   F = 64° C.

The intermediate acids VI b, c and d are prepared by the previous method of operation starting from substituted phenylacetic acids and suitable alkyl halogenides.

VI.b/2-p.toluyl butanoic acid
(R1 = p.CH3—C6H4; R2 = C2H5)
Rdt = 89%   F = 62° C.

VI.c/3-methyl-2-phenyl butanoic acid
(R1 = C6H5; R2 = (CH3)2—CH)
Rdt = 67%   F = 70° C.

VI.e/2-(3,4-dichloro) phenyl butanoic acid
(R1 = 3,4-Cl2—C6H3; R2 = C2H5)

100.0 g (0.537 mol) of 3,4-dichloro phenylacetonitrile at approximately 5° C. is introduced into a solution of 59.2 g (1.48 mol) of soda in pastilles in 60 ml of water in a reactor stirring vigorously then adding 1.2 g (52 mmol) of benzyltriethyl ammonium chloride. The mixture is kept at 5° C. for 10 minutes then when returning to ambient temperature, 50.3 g (0.462 mol) of ethyl bromide is added in approximately 40 minutes and at 20° C.

The mixture which has a red colour is stirred for 4 hours then left overnight at 4° C.

After adding 560 ml of water, the benzane is extracted. The collected organic phases are washed by a saturated sodium chloride solution. The benzane is evaporated, the intermediate nitrile VII.e obtained is purified by distillation:

Eb/0.2 = 110-120 C.
Weight = 100.0 g   Rdt = 87%

100.0 g (0.47 mol) of the VII.e nitrile and 21.5 ml of absolute ethanol are saturated at −15° C. by a current of gaseous hydrobromic acid in an anhydrous atmosphere. After one night at ambient temperature 880 ml of acetone is added then heated and taken to reflux for one hour. The solution is concentrated in the boiler and under a vacuum then 800 ml of concentrated sodium hydroxide solution at 30% w/v is added to the oily residue and stirred at reflux and continuing to stir for 30 hours.

The mixture is cooled, extracted in chloroform, the alkaline aqueous phase is acidified while cold to a pH of 1 by a concentrated solution of sulphuric acid diluted to half.

The solvents are evaporated after extraction with chloroform and the organic phases treated in the conventional manner and the residue obtained crystallised for purification in 300 ml of petroleum ether.

Weight = 80.0 g   Rdt = 74%   F = 82° C.

The VI.f and VI.g acids have been prepared by this method via their corresponding VII.f and VII.g nitriles.

VI.f/2-p.chlorophenyl butanoic acid
(R1 = p.Cl—C6H4; R2 = C2H5)
VII.f nitrile:   Rdt = 82%   Eb/0.05 - 85-95° C.
VI.f acid:   Rdt = 65%   F = 84° C.

VI.g/2-(m.trifluoromethyl) phenyl butanoic acid
(R1 = m.F3C—C6H4; R2 = C2H5)
VII.g nitrile:   Rdt = 58%   Eb/0.06 = 75-80° C.
VI.g acid:   Rdt = 77%   F = 72° C.

Products of structures (V)

V.a/1-(3-bromo-1-propenyl)-3,4-dichlorobenzene
(R5 = 3.4 Cl2—C6H3; Q = —CH=CH—   Z7 = Br)

100.6 g (0.46 mol) of dichlorocinnamic acid is suspended in 1700 ml of methanol in a reactor protected from humidity and in a nitrogen atmosphere.

After adding 56.6 ml of complex BF3 - ether (65.3 g, 0.46 mol) the mixture is brought to reflux by stirring for 18 hours. The solution is evaporated, the residue recovered by approximately 1 l of dichloromethane, the solution obtained washed with a saturated sodium bicarbonate solution then with water. After distillation the residue is purified by crystallisation in ethanol. 99.2 g of 3,4-methyl dichlorocinnamate is obtained in the form of white crystals.

Rdt = 93%   F = 115° C.

· 300 g of a toluene solution (1.5M of DIBAL-H(R)) is added to 5.0 g (0.24 mol) of the previous ester in 540 ml of toluene at −40° C. and in approximately 1 hour in a nitrogen atmosphere. The mixture is kept at −0° C. for 2 hours 30 minutes then 1 liter of sulphuric acid solution approximately 2M is carefully introduced after returning to a temperature of approximately 10° C. The toluene phase is separated, the acid phase extracted in ether. The connected organic phases are washed by a saturated sodium bicarbonate solution then dried on Na2SO4.

The solvents are eliminated by distillation and the residue purified by chromatography on a column.

The elution by means of the 80/20 dichloromethane acetone mixture followed by crystallisation in hexane will make it possible to obtain 47.9 g (Rdt=97%) of purified 3,4-dichlorocinnamic alcohol F=64° C.

A solution of 25.1 g (0.29 mol) of lithium bromide is introduced in 225 ml of acetonitrile in a reactor protected from humidity and in a nitrogen atmosphere.

Then at 40° C. while stirring, add successively 39.3 g (0.36 mol) of chlorotrimethylsilane in 30 minutes and then 29.45 g (0.145 mol) of 3,4-dichlorocinnamic alcohol in solution in 125 ml of acetonitrile. The mixture is kept at reflux for 16 hours while stirred then cooled and precipitated in 400 ml of ether and 250 ml of icy water. The separated organic phase is washed by a saturated sodium bicarbonate solution then by a saturated NaCl solution. The solvents are eliminated and the rough residual product purified by distillation.

| Weight = 35.1 g | Rdt = 91% | Eb/0.1 = 115-120° C. |
|---|---|---|
| V.b/1-(3-chloro 1-propenyl)-3,4,5 trimethoxybenzane | | |
| (R5 = 3,4,5(CH3O)3—C6H2; Q = —CH=CH— Z7 = Cl) | | |

A suspension of 22.0 g (0.58 mol) of lithium aluminum hydride in 300 ml of THF is gradually introduced in a suspension of 25.7 g (0.193 mol of aluminum chloride in 300 ml of ether at a temperature of −10° C. and in a nitrogen atmosphere. 73.0 g (0.290 mol) of 3-(3,4,5-trimetoxyphenyl)-2-methyl propenate in solution in 280 ml of THF is introduced in 10 minutes at the same temperature. The mixture is then stirred for 15 minutes then precipitated in an icy solution of sulphuric acid 2.5M, extracted by ether. The collected organic phases are washed, dried. The evaporation of the solvents lead to 3,4,5-trimetoxycinammomic alcohol which is used as it is.

A solution of 62.6 g (0.279 mol) of the previous alcohol in 500 ml of dichloromethane is cooled in an iced water bath. 20.4 g of 4-dimethylaminopyridine, 63.9 g of p.toluene-sulphochloride and 38.9 ml of triethylamine are added to it successively and stirred. The solution is kept at ambient temperature for 1 hour while stirred, then diluted by the addition of 1 liter of ether. The suspension is filtered, the organic phase extracted in a solution of 10% (w/v) of copper sulphate, then in a saturated sodium bicarbonate solution and finally with a saturated sodium chloride solution. After drying and evaporating the ether, 49.7 g (71%) of yellow orange oily product is obtained (unstable) and is used immediately as it is for the continuation of the synthesis.

| V.c/1-(2-thienyl)-3-chloroprop-1-ene |
|---|
| (R5 = 2-thienyl; Q = —CH=CH—; Z7 = Cl) |

1st stage: heat 104.06 g (1.0 mol) of malonic acid, 56.07 g (0.50 mol) of 2-thiophenecarboxaldehyde, 250 ml of pyridine and 5 ml of piperidine in the water bath for 2 hours then in the reflux for 5 minutes. Precipitate the solution in water after cooling and treat with an excess of hydrochloric acid (250 ml of concentrated solution at 37%) to obtain a precipitate. Filter the insoluble parts and then recrystallise in a mixture of ethanol-water to obtain purified 2-thienylacrylic acid.

| Weight = 42.38 g | Rdt = 58% | F = 143-144° C. |
|---|---|---|

2nd stage: heat 37.45 g (0.24 mol) of the acid above, 30 ml (0.24 mol) of complex BF3-ether in 310 ml of methanol in the reflux for 6 hours. Precipitate the cooled solution in water and then extract it in dichloromethane. Combine the organic extraction phases, wash with a saturated NaHCO3 solution then with a saturated NaCl solution then dehydrate it on MgSO4. Recrystallise the brown solid residue obtained after eliminating the solvents by distillation in hexane to obtain the purified methyl 2-thienylacrylate.

| Weight = 32.65 g | Rdt = 86% | F = 46-47° C. |
|---|---|---|

3rd stage: add a suspension of 4.51 g (118.9 mmol) of lithium aluminum hydride in 150 ml of THF to a mixture of 5.28 g (39.6 mmol) of aluminum chloride and 40 ml of diethyl ether cooled to −10° C. and stir gently under a nitrogen atmosphere.

Gently add a solution of 10.0 g (59.45 mmol) of methyl ester above in 50 ml of THF at −10° C. then stir the solution at the same temperature for one hour and a half. Break down the complexes of the solution by adding a 3M sulphuric acid solution and the mixture extracted to the ether. Wash the combined etherised phases by a saturated NaHCO3 solution then by a saturated NaCl solution and dehydrate on MgSO4. 7.83 g (94%) of residual product in the form of a brown oil is obtained by evaporating the ether under a vacuum. Preserve the coarse 1-(2-thienyl)-1-propen-3-ol which is unstable at ambient temperature at a temperature below 0° C.

4th stage: gently add 21.74 ml (296 mmol) of dimethyl sulphur to a mixture of 39.53 g (296 mmol) of N-chlorosuccinimide in 180 ml of anhydrous dichloromethane at a temperature of 0° C. Cool the mixture to −10° C. and add a solution of 11.86 g (84.6 mmol) of the above alcohol in 50 ml of dichloromethane.

Return the temperature of the solution to 0° C. and maintain it there for 2 hours. Dilute the mixture by 100 ml of hexane then precipitate in 200 ml of iced water. Separate the organic phase and re-extract the aqueous phase with ether. Wash the combined etherised phases then dehydrate. Eliminate the ether by distillation in a vacuum to obtain the coarse 1-(2-thienyl)-3-chloroprop-1-ene in the form of unstable brown oil which is used just as it is.

| Weight = 12.06 g | Rdt = 94% |
|---|---|
| V.d/1-(3-thienyl)-3-chloroprop-1-ene | |
| (R5 = 3-thienyl; Q = —CH=CH—; Z7 = Cl) | |

The intermediate product is obtained starting from the 3-thiophenecarboxaldehyde by the process described in the preceding example.

1st stage: 3-thienylacrylic acid
F=146° C. (ethanol/water)

2nd stage: methyl 3-thienylacrylate
F=49° C. (hexane)
3rd stage: 1-(3-thienyl)-1-propen-3-ol unpurified oil
4th stage: 1-(3-thienyl)-3-chloroprop-1-ene unpurified amorphous white solid.

V.e/1-(2-furyl)-3-chloroprop-1-ene
(R5 = 2-furyl; Q = —CH=CH—; Z7 = Cl)

The intermediate product is obtained starting from 2-furylcarboxaldehyde in four stages in accordance with the process described when preparing the V.c intermediate product.

V.f/trans-1-mesyloxymethyl-2-phenylcyclopropane
(R5 = C6H5; Z7 = CH3—SO3; Q = cyclopropene 1,2 diyl)

1st stage: add a solution of 25.0 g (154 mmol) of trans-2-phenylcyclopropanecarboxylic acid in 100 ml of THF to a boron complex borane-THF solution drop by drop under a nitrogen atmosphere. Place the solution in the reflux for 3 hours and gently add 130 ml of NaOH 2N solution and stir the mixture for 30 minutes. Concentrate the etherised extracts in a vacuum to obtain 20.78 g of coarse trans-1-hydroxymethyl-2-phenylcyclopropane which is purified by distillation.

| Weight = 18.19 g | Rdt = 80% | Eb/0.25 = 90-97° C. |

2nd stage: add 9.18 g (66.2 mmol) of the alcohol obtained above and 13.89 ml (99.25 mmol) of triethylamine into 100 ml of dichloromethane. Add 5.63 ml (72.8 mmol) of methane sulfonyl chloride drop by drop under a nitrogen atmosphere and at −10° C. Stir the mixture for 15 minutes at −10° C. then wash successively with iced water with a 10% HCl solution, a saturated NaHCO3 solution then with a saturated NaCl solution. Concentrate the solution in a vacuum after dehydrating on MgSO4 at 0° C. to obtain a yellow oil. Dissolve the intermediate product V.f obtained in this manner in the anhydrous THF and use as it is.

V.g/trans-1-bromomethyl-2-phenylcyclopropane
(R5 = C6H5; Z7 = Br; Q = cyclopropene 1,3 diyl)

Add 61.0 g (0.34 mol) of N-bromosuccinimide to 300 ml of dichloromethane and cool to 0° C. under a nitrogen atmosphere then add drop by drop 29.4 ml (0.41 mol) of dimethyl sulphide. Stir the mixture at 0° C. for 30 minutes then cool to 625° C.; then introduce a solution of 33.6 g (0.23 mol) of trans-2-phenyl-1-cyclopropane methanol drop by drop obtained when preparing the V.f in 100 ml of methyl chloride. Stir the mixture for 6 hours at 0° C. then 16 hours at 25° C.; then dilute by adding 250 ml of hexane and the mixture precipitated in 250 ml of iced water. Wash the organic phase with a saturated NaCl solution then dehydrate on MgSO4. Eliminate the solvents by concentrating in a vacuum and purify the residue by distillation.

| Weight = 40.81 g | Rdt = 85% | Eb/0.2 = 72° C. |

V.h/trans-1-mesyloxymethyl-2-(3,4,5-trimethoxyphenyl)cyclopropane
(R5 = 3,4,5(CH3O)3-C6H2; Z7 = CH3-SO3; Q = cyclopropene 1,2 diyl)

1st stage: add 55.0 g (0.23 mol) of 3,4,5-trimethyoxycinnamic acid and 28.39 ml (0.23 mol) of BF3 - ether complex to 400 ml of methanol, heat the solution for 6 hours in the reflux. Cool the mixture then precipitate in water and extract in dichloromethane. Treat and dessicate the combined organic phases then eliminate the solvent by distillation in a vacuum. Purify the methyl 3,4,5-trimethoxycinnamate by recrystallisation in methanol.

| Weight = 46.17 g | Rdt = 80% | F = 96-98° C. |

2nd stage: gently add 106.83 ml (213.7 mmol) of N-butyllithium in 2M solution in hexane to a solution of 20.15 ml (214 mmol) of 2-methyl-2-propanol in 125 ml of anhydrous CHF. After 30 minutes treat the solution by adding drop by drop a solution in 100 ml of THF of 17.97 g (71.22 mmol) of methyl ester above. Place the reactive medium in the reflux for two and a half hours then cool in an ice bath and hydrolise by adding 200 ml of water. Extract the aqueous phase in ethyl acetate and dehydrate the organic fractions on MgSO4. Evaporate the solvents in a vacuum to produce a residue of t.butyl 3,4,5-trimethoxycinnamate, which is purified by recrystallisation of the hexane.

| Weight = 16.27 g | Rdt = 78% | F = 83-85° C. |

3rd stage: Add 3.0 g of sodium hydride in oily dispersion at 60% (75 mmol) to a stirred suspension of 15.47 g (70.3 mmol) of trimethylsulphonium iodide in 150 ml of DMSO which is held at 25°-30° C. under a nitrogen atmosphere.

After the hydrogen has been released (approx. 30 minutes) add a solution of 15.9 g (54 mmol) of t.butylic ester above in 100 ml of DMSO solution without exceeding 35° C.

Stir the mixture for 30 minutes at 25°-30° C. then one and a half hours at 55°-60° C. Then precipitate in 380 ml of water and extract by ethyl acetate. Dehydrate and concentrate the combined extracts in a vacuum to obtain the t.butyl trans-2-(3,4,5-trimethoxyphenyl) cyclopropanecarboxylate residue in the form of a yellow oil which solidifies. Purify the product by recrystallisation of the hexane.

| Weight = 9.69 g | Rdt = 58% | F = 68-70° C. |

4th stage: disperse 3.66 g (96.5 mmol) of lithium aluminum hydride in 150 ml of THS under a nitrogen atmosphere. Gently add 9.92 g (32.2 mmol) of t.butylic ester above in solution in 100 ml of THF. Heat the mixture in the reflux for one and a half hours then carefully add 5.58 ml of 10% NaOH solution then 7.32 ml of water. Keep the suspension obtained stirred during one night; filter the insoluble part and the filtrate concentrated in a vacuum to obtain the coarse trans-1-(hydroxymethyl)-2-(3,4,5-trimethoxyphenyl)cyclopropane, which is purified by distillation in a vacuum.

| Weight = 6.65 g | Rdt = 87% | Eb/0.02 = 145–165° C. |

5th stage: proceed as described in stage 2 of the preceding intermediate product V.f with the derivative obtained above to obtain the trans-1-mesyloxymethyl-2-(3,4,5-trimethoxyphenyl) cyclopropane in the form of a white solid and use it without any further purification.

Intermediate products of structure (III)

| III.a/ã-cinnamyl-ã-ethyl-phenylacetic acid |
| (R1 = R5 = C6H5; R2 = C2H5); Q = —CH=CH— |

A solution of 339 g of diisopropylamine (3.35 mol) in 2.2 l of anhydrous THF in a 12 liter reactor protected from humidity and in a nitrogen atmosphere is cooled to −10° C. 330 ml of butyl lithium solution 10M in hexane (3.30 mol) is added gently and at a temperature less than −10° C. The solution is kept at this temperature for 30 minutes then a solution of 250 g (1.52 mol) of 2-phenyl butanoic acid in 300 ml of THF is added allowing the temperature to rise progressively to 15° C. It is then heated to 55°–60° C. for 3 hours, cooled to 5° C. and 300 g (1.52 mol) of cinnamyl bromide in solution in 250 ml of THF is introduced without exceeding 15° C.

It is kept at the laboratory temperature for 18 hours while being stirred then without exceeding 30° C., 2 l of 3N HCl solution is added followed by 1 l of water; 1.5 l of ethyl acetate is extracted twice, 4 l of hexanes added to the collected extraction phases, the mixture washed twice in 1.2 l of N NaOH solution. The alkaline aqueous phases are acidified by a concentrated solution of HCl then extracted twice to 1.5 l of ethyl acetate. The organic phases are collected and washed with a saturated sodium chloride solution then concentrated by distillation.

The rough residual product obtained (428 g) is purified by crystallisation in 2 l of hexane-ethyl acetate 3/1 v/v mixture. The product is obtained in the final form of white crystals.

| Weight = 320 g | Rdt = 75% |
| F = 134–136° C. | CCM: 0.40; S.C. |

Starting from cinnamyl bromide and intermediate acids with VI structure as described previously, the derived products III.b to III.f are prepared by the method of operation of example III.a.

| III.b/ ã-cinnamyl-ã-ethyl-p.chlorophenylacetic acid |
| (R1 = p.Cl-C6H4; R2 = C2H5; R5 = C6H5; Q = —CH=CH—) |
| Rdt = 86% F = 185° C. (ether) CCM: 0.40; S.H. |
| III.c/ ã-cinnamyl-ã-ethyl-(3,4-dichloro)phenyl acetic acid |
| (R1 = 3,4 Cl2-C6H3; R2 = C2H5; R5 = C6H5; Q = —CH=CH—) |
| Rdt = 72% F = 125° C. (petroleum ether) CCM: 0.55; S.J. |
| III.d/ ã-cinnamyl-ã-ethyl-p.tolylacetic acid |
| (R1 = p.CH3-C6H4; R2 = C2H5; R5 = C6H5; Q = —CH=CH—) |
| Rdt = 72% F = 169° C. (ether) CCM: 0.45; S.H. |
| III.e/ ã-cinnamyl-ã-ethyl-(3-trifluoromethyl phenylacetic acid |
| (R1 = m.F3C-C6H4; R2 = C2H5; R5 = C6H5; Q = —CH=CH—) |
| III.f/ ã-cinnamyl-ã-ethyl-p.metoxyphenylacetic acid |
| (R1 = p.CH3O-C6H4; R2 = C2H5; R5 = C6Hr; Q = —CH=CH—) |
| Rdt = 54% F = 147° C. (ether) CMCM: 0.40; S.H. |

The process of example III.a applied to 1-(3-bromo-1-propenyl) 3,4-dichlorobenzane (agent V.a) with (VI) intermediate acids enables the III.g to III.m compounds to be obtained.

| III.g/ ã-(3',4'-dichloro) cinnamyl-ã-methylacetic acid |
| (R1 = C6H5; R2 = CH3; R5 = 3,4 Cl2-C6H3; Q = —CH=CH—) |
| Rdt = 61% F = 116° C. (hexanes) CCM: 0.50; S.I. |
| III.h/ ã-(3',4'-dichloro) cinnamyl-ã-ethylphenylacetic acid |
| (R1 = C6H5; R2 = C2H5; R5 = 3,4 Cl2-C6H3; Q = —CH=CH—) |
| Rdt = 58% F = 121° C. (hexanes) CCM: 0.45; S.C. |
| III.i/ ã-(3',4'-dichloro) cinnamyl-ã-isopropylphenylacetic acid |
| (R1 = C6H5; R2 = (CH3)2-CH; R5 = 3,4 Cl2-C6H3; Q = —CH=CH—) |
| Rdt = 69% F = 115° C. (petroleum ether) CCM: 0.45; S.H. |
| III.j/ ã-(3',4'-dichloro) cinnamyl-ã-ethyl-p.tolylacetic acid |
| (R1 = p.CH3-C6H4; R2 = C2H5; R5 = 3,4 Cl2-C6H3; Q = —CH=CH—) |
| Rdt = 72% F = 105° C. (ethyl acetate) CCM: 0.30; S.E. |
| III.k/ ã-(3',4'-dichloro) cinnamyl-ã-ethyl-p.metoxyphenylacetic acid |
| (R1 = p.CH3O-C6H4; R2 = C2H5; R5 = 3,4 Cl2-C6H3; Q = —CH=CH—) |
| Rdt = 70% F = 135° C. (petroleum ether) CCM: 0.60; S.J. |
| III.l/ ã-(3',4'-dichloro) cinnamyl-ã-ethyl-p.chlorophenylacetic acid |
| (R1 = p.Cl-C6H4; R2 = C2H5; R5 = 3,4 Cl2-C6H3; Q = —CH=CH—) |
| Rdt = 70% F = 160° C. (petroleum ether) CCM: 0.60; S.L. |
| III.m/ ã-(3',4'-dichloro) cinnamyl-ã-ethyl-(3-trifluoromethyl) phenylacetic acid |
| (R1 = m.F3C-C6H4; R2 = C2H5; R5 = 3,4 Cl2-C6H3; Q = —CH=CH—) |
| Rdt = 62% F = 96° C. (hexanes) CCM: 0.40; S.L. |

PRODUCTS OF THE INVENTION: EXAMPLES

Example 1; benzylisocyanates of formula (II.1)

The products of the invention of examples 1.a. to 1.m below are prepared by Curtius reaction in one stage starting from acids of the formula (III) previously described. The isocyanates (II.1), which are unstable, are purified by chromatography. They are viscous oils where the purity and the identity are verified by the analyses already described. Among other things, and more particularly, these compounds produce a characteristic band of the isocyanate functions at 2200–2300 cm$^{-1}$ when subjected to infrared spectrography.

Method of operation:

Add 1.0 mol of acid (III) to be treated, 162.5 g (2.5 mol) of sodium azide and 197.75 g (202 ml, 2.5 mol) of pyridine to 8 liters of dichloromethane in a reactor protected from humidity. Introduce phenyldichlorophosphate drop by drop in 15 minutes while stirring and at ambient temperature. Stir the mixture at the laboratory temperature for 18 to 20 hours then extract successively with water then with 0.1N HCl. Dry the organic phase on sodium sulphate, filtrate and then add 5 liters of toluene to the filtrate; distill the solution at ordinary pressure to eliminate the dichloromethane. Heat the toluene residue very gradually and raise to reflux taking between 45 minutes and 2 hours, until the gaseous release is ended. After cooling, add hexanes, filter the mixture, then eliminate the solvents by distillation in a vacuum and in a boiler. Purify the coloured oily residue by chromatography.

Example 1.a: ã-cinnamyl- ã-ethyl-benzylisocyanate (II.1: R1 = R5 = C6H5; R2 = C2H5; Q = —CH=CH—)
Rdt = 94%   CCM: 0.45–0.55; S.C.
RMN: 0.80 (t,3H); 2.00 (q,2H); 2.80 (d,2H); 6.00 (m,1H); 6.50 (m,1H); 7.25 (m,5H); 7.35 (m,5H).

Example 1.b: ã-cinnamyl-ã-ethyl-p.chlorobenzylisocyanate (II.1; R1 = p.Cl-C6H4; R2 = C2H5; R5 = C6H5;
Q = —CH=CH—)
Rdt = 86%   CCM: 0.75–0.86; S.F.
RMN: 0.80 (t,3H); 1.95 (q,2H); 2.75 (d,2H); 5.70–6.60 (m,2H); 7.15–7.40 (m,9H)

Example 1.c: ã-cinnamyl-ã-ethyl-(3,4-dichloro)benzylisocyanate (II.1; R1 = 3,4 Cl2-C6H4; R2 = C2H5; R5 = C6H5;
Q = —CH=CH—)
Rdt = 77%   CCM: 0.30–0.40; S.F.
RMN: 0.80 (t,3H); 1.95 (q,2H); 2.75 (d,2H); 5.70–6.60 (m,2H); 7.00–7.50 (m,8H)

Example 1.d: ã-cinnamyl-ã-ethyl-p.methylbenzylisocyanate (II.1; R1 = p.CH3-C6H4; R2 = C2H5; R5 = C6H5;
Q = —CH=CH—)
Rdt = 97%   CCM: 0.80–0.90; S.G.
RMN: 0.80 (t,3H); 2.00 (q,2H); 2.35 (s,3H); 2.85 (d,2H); 5.65–6.70 (m,2H); 7.00–7.40 (m,9H)

Example 1.e: ã-cinnamyl-ã-ethyl-m.(trifluoromethyl) benzylisocyanate (II.1; R1 = m.F3C-C6H4; R2 = C2H5; R5 = C6H5;
Q = —CH=CH—)
Rdt = 89%   CCM: 0.75–0.85; S.G.
RMN: 0.80 (t,3H); 2.00 (q,2H); 2.80 (d,2H); 5.75–6.60 (m,2H); 7.10–7.65 (m,9H)

Example 1.f: ã-cinnamyl-ã-ethyl-p.metoxybenzylisocyanate (II.1; R1 = p.CH3O-C6H4; R2 = C2H5; R5 = C6H5;
Q = —CH=CH—)
Rdt = 96%   CCM: 0.75–0.85; S.G.
RMN: 0.80 (t,3H); 2.00 (q,2H); 2.80 (d,2H); 3.80 (s,3H); 5.80–6.70 (m,2H); 6.80–7.50 (m,9H)

Example 1.g: ã-(3',4'-dichloro) cinnamyl-ã-methyl-benzylisocyanate (II.1; R1 = C6H5; R2 = CH3; R5 = 3,4 Cl2-C6H3;
Q = —CH=CH—)
Rdt = 93%   CCM: 0.55–0.65; S.F.
RMN: 1.75 (t,3H); 2.70 (d,2H); 5.60–6.50 (m,2H); 6.90–7.50 (m,8H)

Example 1.h: ã-(3',4'-dichloro) cinnamyl-ã-ethyl-benzylisocyanate (II.1; R1 = C6H5; RE2 = C2H5; R5 = 3,4 Cl2-C6H3;
Q = —CH=CH—)
Rdt = 78%   CCM: 0.55–0.65; S.F.
RMN: 0.90 (t,3H); 2.25 (m,2H); 3.25–3.90 (m,2H); 6.30 (s,2H); 7.70–7.70 (m,8H)

Example 1.i: ã-(3',4'-dichloro) cinnamyl-ã-isopropylbenzylisocyanate (II.1, R1 = C6H5; R2 = (CH3)2CH; Q = —CH=CH—)
R5 = 3,4 Cl2-C6H3)
Rdt = 75%   CCM: 0.45–0.55; S.F.
RMN: 0.30–1.25 (m,7H); 2.35–2.90 (m,2H); 5.70–6.65 (m,2H); 6.75–7.40 (m,8H)

Example 1.j: ã-(3',4'-dichloro) cinnamyl-ã-ethyl-p.methylbenzylisocyanate (II.1, R1 = p.CH3-C6H4; R2 = C2H5; R5 = 3,4 Cl2-C6H3;
Q = —CH=CH—)
Rdt = 91%   CCM: 0.85; S.F.
RMN: 0.75 (t,3H); 1.95 (q,2H); 2.25 (s,3H); 2.70 (d,2H), 5.60–6.35 (m,2H); 6.90–7.30 (m,7H)

Example 1.k: ã-(3',4'-dichloro) cinnamyl-ã-ethyl-p.metoxybenzylisocyanate (II.1, R1 = p.CH3O-C6H4; R2 = C2H5; R5 = 3,4 Cl2-C6H3;
Q = —CH=CH—)
Rdt = 89%   CCM: 0.30; S.F.
RMN: 0.80 (,3H); 2.00 (q,2H); 2.75 (d,2H); 3.80 (s,3H); 5.70–6.45 (m,2H); 6.80–7.35 (m,7H)

Example 1.l: ã-(3',4'-dichloro) cinnamyl-ã-ethyl-p.chlorobenzylisocyanate (II.1, R1 = p.Cl-C6H4; R2 = C2H5; R5 = 3,4 Cl2-C6H3;
Q = —CH=CH—)
Rdt = 87%   CCM: 0.50; S.F.
RMN: 0.80 (t,3H); 1.95 (q,2H); 2.75 (d,2H); 5.70–6.45 (m,2H); 6.90–7.60 (m,7H)

Example 1.m: ã-(3',4'-dichlorocinnamyl-ã-ethyl-m.trifluoromethylbenzylisocyanate (II.1, R1 = m.F3C-C6H4; R2 = C2H5; R5 = 3,4 Cl2-C6H3;
Q = —CH=CH—)
Rdt = 86%   CCM: 0.40; S.F
RMN: 0.85 (t,3H); 2.05 (q,2H); 2.80 (d,2H); 5.70–6.45 (m,2H); 6.95–7.70 (m,7H)

Example 2: ã-alkyl-ã-amino phenylacetonitriles of formula (II.3)

The compounds are prepared by alkylation of the phenyl acetonitriles (X) with the reagents (V) of which the agents have been previously described in the preparations of V.a to V.h.

After reaction, the compounds obtained, which are unstable, are either purified by crystallisation or used as they are in the remainder of the reactions.

The purity and the identity of the products are verified by chromatography on soft layers and by RMN.

Method of operation:

Add 1.025 mole of n. butyllithium (solution 10M/hexanes) drop by drop at −20° C. into a solution of 1.025 mole of diisopropyl in 1 liter of anhydrous tetrahydrofurane in a reactor protected from humidity and in a nitrogen atmosphere. Keep the mixture at −20° C. for 15 minutes. At −72° C. introduce 1 mole of nitrile (X) in solution in 200 ml of THF, and continue to stir for 1 hour 30 minutes at this temperature then add 1.025 mole of halogen derivative (V) in solution in 500 ml of THF. After 20 minutes at −72° C., stir the mixture for 1 hour at ambient temperature.

Then add 1.5 l of NH4Cl solution at 10% (w/v) and 750 ml of 1-1 (v/v) hexaneethylacetate mixture.

Separate the organic phase, reextract the aqueous phase by the same mixture of solvents. Wash the collected organic phases by extraction with a saturated sodium chloride solution, then dry on MgSO4. Eliminate the solvents by distillation in a vacuum and in a boiler. As the case may be, crystallise the oily residue by adding hexanes, or use as it is in reaction i.1 described in diagram 1.

Depending on the method of operation and by alkylation of the compounds suitable halogen derivatives (V), prepare the products of example 2.a to 2.g and 2.m to 2.s.

Example 2.a: ã-cinnamyl-ã-dimethylamino-phenylacetonitrile (II.3; R1 = R5 = C6H5; R3 = R4 = CH3)
Rdt = 68% (coarse) CCM: 0.40–0.50; S.C.
RMN: 2.30 (s, 6H); 2.85 (m, 2H); 5.55–5.90 (m, 1H); 6.10–6.50 (m, 1H); 7.00–7.70 (m, 10H)

Example 2aa: trans-ã-dimethylamino-ã-(2-phenyl-1-cyclopropylmethyl)-phenylacetonitrile (II.3, R1 = R5 = C6H5; R3 = R4 = (H3, Q = cyclopropylene 1,2 diyl)
Rdt = 57% (coarse) CCM: 0.65–0.70; S.G.
RMN: 0.60–0.90 (m, 3H); 1.28 (m, 1H); 2.15 (m, 2H); 2.30 (d, 6H); 6.78–7.78 (m, 10H)

Example 2.b: ã-cinnamyl-ã-dimethylamino-p.chlorophenylacetonitrile (II.3; R1 - p.Cl—C6H4; R3 = R4 = CH3; R5 = C6H5; Q = —CH=CH—)

-continued

Rdt = 70% (coarse) CCM: 0.70-0.80; S.G
RMN: 2.35 (s, 6H); 2.85 (m, 2H); 5.45-5.85 (m, 1H); 6.20-6.40 (m, 1H); 7.10-7.60 (m, 9H)

Example 2.c: ã-cinnamyl-ã-dimethylamino-3,4-dichlorophenyl-acetonitrile
(II.3; R1 = 3,4Cl2—C6H3; R3 = R4 = CH3; R5 = C6H5; Q = —CH=CH—)
Rdt = 85% F = 88° C. (hexanes) CCM: 0.85-0.95; S.J.
RMN: 2.30 (s, 6H0; 2.80 (m, 2H); 5.50-5.90 (m, 1H); 6.15-6.40 (m, 1H); 7.15-78.50 (m, 8H)

Example 2.d: ã-cinnamyl-ã-dimethylamino-p.methylphenylacetonitrile
(II.3; R1 = p.CH3—C6H4; R3 = R4 = CH3; R5 = C6H5; Q = —CH=CH—)
Rdt = 86% CCM: 0.25-0.35; S.G
F = 85° C. (hexanes)
RMN: 2.35 (s, 6H); 2.65-3.15 (m, 2H); 5.50-5.85 (m, 1H); 6.25-6.40 (m, 1H); 7.10-7.50 m, 9H).

Example 2.e: ã-cinnamyl-ã-dimethylamino-p.trifluoromethyl-phenyl-acetonitrile
(II.3; R1 = p.F3C—C6H4; R3 = R4 = CH3; R5 = C6H5; Q = —CH=CH—)
Rdt = 99% (coarse) CCM: 0.70-0.80; S.G
RMN: 2.35 (s, 6H); 2.90 (m, 2H); 5.45-5.85 (m, 1H); 6.15-6.40 (m, 1H); 7.10-7.45 (m, 5H); 7.55-7.80 (m, 4H)

Example 2.f: ã-cinnamyl-ã-dimethylamino-p.metoxyphenylacetonitrile
(II.3; R1 = p.CH30—C6H4; R3 = R4 = CHJ3; R5 = C6H5; Q = —CH=CH—)
Rdt = 85% F = 77° C. (hexanes) CCM: 0.85-0.95; S.G
RMN: 2.25 (s, 6H); 2.90 (m, 2H); 3.85 (s, 3.H); 5.50-5.85 (m, 1H); 6.20-6.45 (m, 1H); 6.80-7.55 (m, 9H).

Example 2.g: ã-(3',4'-dichloro)cinnamyl-ã-dimethylaminophenyl acetonitrile
(II.3; R1 - C6H5; R3 = R4 = CH3; R5 = 3,4 Cl2=C6H3; Q = —CH=CH—)
Rdt = 78% (coarse) CCM: 0.35-0.45; S.C.
RMN: 2.25 (s, 6H); 2.85 (d, 2H); 6.05-6.50 (m, 2H); 7.05-7.55 (m, 8H).

Example 2.h: trans-ã-dimethylamino-ã-(2-phenyl-1-cyclopropylmethyl)-(3,4,5-trimethoxyphenyl)acetonitrile
(II.3; R1 = 3,4,5(CH30)3—C6H2; R3 = R4 = CH3; R5 = C6H5; Q = cyclopropylene 1,2 diyl)
Rdt = 87% (coarse) CCM: 0.50-0.55; S.D.
RMN: 0.60-0.80 (m, 2H); 1.10-1.30 (m, 1H); 1.60-1.90 (m, 1H); 2.28 (d, 8H); 3.86 (m, 9H); 6.78 (d, 2H); 6.89-7.39 (m, 5H)

Example 2.i: ã-dimethylamino-ã-[(2-thienyl)-2-propenyl]-phenyl acetonitrile
(II.3; R1 = C6H5; R3 = R4 = CH3; R5 = 2-thienyl; Q = —CH=CH—)
Rdt = 80% (coarse) CCM: 0.07; S.D.
RMN: 2.23 (s, 6H); 2.80 (d, 2H); 5.88-6.19 (dt, 1H); 6.60 (d, 1H); 6.87-7.38 (m, 8H)

Example 2.j: ã-dimethylamino-ã-[(3-thienyl)-2-propenyl]-phenyl acetonitrile
(II.3; R1 = C6H5; R3 = R4 = CH3; R5 = 3-thienyl; Q = —CH=CH—)
Rdt = 75% (coarse) CCM: 0.60; S.A>
RMN: 2.30 (s, 6H); 2.85 (m, 2H); 5.40 (m, 1H); 6.30 (d, 1H); 6.90-7.80 (m, 8H)

Example 2.m: ã-dimethylamino-ã-(3',4',5' trimethoxy) cinnamyl-phenylacetonitrile
(II.3; R1 = C6H5; R3 = R4 = CH3; R5 = 3,4,5 (CH30)3—C6H2; Q = —CH=CH—)
Rdt = 85% (coarse) CCM: 0.45-0.55; S.E.
RMN: 2.25 (s, 6H); 2.75-3.05 (m, 2H); 3.90 (s, 9H); 6.10-6.45 (m, 2H); 6.60 (s, 2H); 7.20-7.65 (m, 5H)

Example 2.ma: ã-dimethylamino-ã-[20(3',4',5'-trimethoxyphenyl)-1-cyclopropylmethyl]-phenyl acetonitrile
(II.3; R1 = C6H5; R3 = R4 = CH3; R5 = 3,4,5 (CH30)3—C6H2; Q = cyclopropylene 1,2 diyl)
Rdt = 78% (coarse) CCM: 0.35-0.40; S.D.
RMN: 0.55-1.45 (m, 4H); 2.20 (d, 2H); 2.35 (s, 6H); 3.85 (s, 9H); 6.28 (s, 2H); 7.50 (m, 5H)

Example 2.n: ã-(N-allyl-N-methyl)amino-ã-cinnamylphenyl acetonitrile
(II.3; R1 = R5 = C6H5; R3 = CH3; R4 = CH2—CH=CH2; Q = —CH=CH—)
Rdt = 99% (coarse) CCM: 0.55-0.65; S.C.
RMN: 2.35 (s, 3H); 2.85 (d, 2H); 3.10 (d, 2H); 4.95-6.60 (m, 5H); 7.10-7.60 (m, 10H)

Example 2.o: ã-(N-allyl-N-methyl)amino-ã-(3',4' dichloro)cinnamyl-phenylacetronitrile
(II.3; R1 = C6H5; R3—CH3; R4 = CH2—CH=CH2; R5 = 3,4Cl2—C6H3; Q = —CH=CH—)
Rdt = 88% (coarse) CCM: 0.80-0.90; S.C.
RMN: 2.30 (s, 3H); 2.85 (t, 2H); 3.05 (d, 2H); 4.90-6.30 (m, 5H); 7.00-7.60 (m, 8H).

Example 2.p: ã-(3',4'-dichloro)cinnamyl-ã-dimethylamino-p.chlorophenylacetronitrile
(II.3; R1 = p.Cl=C6H4; R3 = R4 = CH3; R5 = 3,4Cl2—C6H3; Q = —CH=CH—)
Rdt = 89% (coarse) CCM: 0.50-0.55; S.C.
RMN: 2.30 (s, 6H); 2.55-3.15 (m, 2H); 5.45-6.35 (m, 2H); 6.85-7.60 (m, 7H)

Example 2.q: ã-(3',4'-dichloro)cinnamyl-ã-dimethylamino-p.methylphenylacetonitrile
(II.3; R1 = p.CH3—C6H4; R3 = R4 = CH3; R5 = 3,4Cl2—C6H3; Q = —CH=CH—)
Rdt = 100% (coarse) CCM: 0.70; S.C.
RMN: 2.30 (s, 9H); 2.50-3.10 (m, 2H); 5.40-6.35 (m, 2H) 6.75-7.50 (m, 7H)

Example 2.r: ã-(3',4'-dichloro)cinnamyl-ã-dimethylamino-p.trifluoromethylphenylacetonitrile
(II.3; R1 = p.F3C—C6H4; R3 = R4 = CH3; R5 = 3,4Cl2—C6H3; Q = —CH=CH—)
Rdt = 100% (coarse) CCM: 0.80-0.90; S.G.
RMN: 2.30 (s, 6H); 2.60-3.15 (m, 2H); 5.40-6.30 (m, 2H); 6.90-7.80 (m, 7H)

Example 2.s: ã-(3',4'-dichloro)cinnamyl-ã-dimethylamino-

-continued p.metoxyphenylacetonitrile (II.3; R1 = p.CH3O—C6H4; R3 = R4 = CH3; R5 = 3.4Cl2—C6H3; Q = —CH=CH—)
Rdt = 82% (coarse) CCM: 0.65–0.70; S.G.
RMN: 2.30 (s, 6H); 2.40—3.15 (m, 2H); 3.80 (s, 3H); 5.45–6.35 (m, 2H); 6.80–7.55 (m, 7H)

Example 2.t: ā-dimethylamino-ā-(2-phenyl-1-cyclopropylmethyl)-2-pyridylacetonitrile (II.3; R1 = 2-pyridyl; R3 = R4 = CH3; R5 = C6H5; Q = cyclopropylene 1,3 diyl)
Rdt = 79% (coarse) CCM: 0.25; S.E.
RMN: 0.62–1.65 (m, 4H); 2.35 (s, 6H); 2.40 (d, 2H); 7.16 (m, 6H); 7.65 (m, 1H); 7.75 (m, 1H); 8.78 (m, 1H)

Example 2.u: ā-cinnamyl-ā-dimethylamino-2-furylacetonitrile (II.3; R1 = 2-furyl; R3 = R4 = CH3; R5 = C6H5; Q = —CH=CH—)
Rdt = 98% (coarse) CCM: 0,50; S.C.
RMN: 0.20–0.85 (m, 5H); 2.31 (m, 2H); 2.45 (s, 3H); 3.00 (d, 2H); 5.81 (dt, 1H); 6.35–6.51 (m, 3H); 7.28 (s, 5H); 7.48 (m, 1H)

Example 2.ua: trans-ā-dimethylamino-ā-(2-phenyl-1-cyclopropy methyl)-2-furylacetonitrile (II.3; R1 = 2-furyl; R3 = R4 = CH3; R5 = C6H5; Q = cyclopropene 1,2 diyl)
Rdt = 91% (coarse) CCM: 0.25–0.30; S.C.
RMN: 0.46–1.43 (m, 4H); 2.17–2.30 (m, 8H); 6.35 (m, 1H); 6.62 (m, 1H); 7.20 (m, 5H); 7.45 (m, 1H)

Example 2.ub: ā-dimethylamino-ā-[3-(2-thienyl)-2-propenyl]-2-furylacentonitrile (II.3; R1 = 2-furyl; R3 = R4 = CH3; R5 = 2-thienyl; Q = —CH=CH—)
Rdt = 96% (coarse) CCM: 0.40–0.45; S.C.
RMN: 2.31 (s, 6H); 2.98 (d, 2H); 5.68 (dt, 1H); 6.31–6.61 (m, 3H); 6.90–7.18 (m, 3H); 7.49 (m, 1H)

Example 2.v: ā-cinnamyl-1-dimethylamino-2-thienyl acetonitrile (II.3; R1 = 2-thienyl; R3 = R4 = CH3; R5 = C6H5; Q = —CH=CH—)
Rdt = 91% (coarse) CCM: 0.45–0.50; S.C.
RMN: 2.45 (s, 6H); 2.88 (d, 2H); 5.82 (dt, 1H); 6.43 (d, 1H); 6.88–7.01 (m, 1H); 7.28 (m, 7H)

Example 2.va: trans-ā-dimethylamini-ā-(2-phenyl-1-cyclopropylmethyl)-2-thienylacetonitrile (II.3; R1 = 2-thienyl; R3 = R4 = CH3; R5 = C6H5; Q = cyclopropene 1,2 diyl)
Rdt = 79% (coarse) CCM: 0.80–0.85; S.D.
RMN: 0.65–1.40 (m, 4H); 2.10–2.25 (m, 2H); 2.37 (s, 6H); 6.73–7.32 (m, 8H)

Example 2.vb: ā-dimethylamino-ā-[3-(2-furyl)-2-propenyl]2-thienyl acetonitrile (II.3; R1 = 2-thienyl; R3 = R4 = CH3; R5 = 2-furyl; Q = —CH=CH—)
Rdt = 79% (coarse) CCM: 0.50; S.C.
RMN: 2.38 (s, 6H); 2.90 (d, 2H); 5.78 (d, 1H); 6.15–6.33 (m, 3H); 6.89–7.05 (m, 1H); 7.20–7.30 (m, 3H)

Example 2.vc: ā-dimethylamini-ā-[3(2-thienyl)-2-propenyl]2-thienyl acetonitrile (II.3; R1 = R5 = 2-thienyl; R3 = R4 = CH3; Q = —CH=CH—)
Rdt = 84% (coarse) CCM: 0.50; S.C.
RMN: 2.38 (s, 6H); 2.80 (d, 2H); 5.67 (dt, 1H); 6.51 (d, 1H); 6.88–7.38 (m, 6H)

Example 2.vd: ā-dimethylamino-ā-[3-(3-thienyl)-2-propenyl]2-thienyl acetonitrile (II.3; R1 = 2-thienyl; R3 = R4 = CH3; R5 = 2-thienyl; Q = —CH=CH—)
Rdt = 87% (coarse) CCM: 0.50; S.C.
RMN: 2.35 (s, 6H); 2.9–3.2 (m, 2H); 5.7 (dt, 1H); 6.45 (d, 1H); 6.85–7.50 (m, 6H)

Example 2.w: ā-cinnamyl-ā-dimethylamino-3-thienyl acetonitrile (II.3; R1 = 3-thienyl; R3 = R4 = CH3; R5 = C6H5; Q = —CH=CH—)
Rdt = 87% (coarse) CCM: 0.40–0.45; S.C.
RMN: 2,35 (s, 6H); 2.5–3.2 (m, 2H); 5.5–6.0 (dt, 1H); 6.3 (d, 1H); 7.3 (s, 5H); 7.0–7.6 (m, 3H)

Example 1.wa: trans-ā-dimethylamino-ā-(2-phenyl-1-cyclopropylmethyl)-3-thienylacetonitrile (II.3; R1 = 3-thienyl; R3 = R4 = CH3; R5 = C6H5; Q = cyclopropene 1,2 diyl)
Rdt = 83% (coarse) CCM: 0.45–0.50; S.B.
RMN: 0.50–2.30 (m, 6H); 2.27 (s, 6H); 6.7–7.5 (m, 8H)

Example 2.wb: ā-dimethylamino-ā-[3-(3-thienyl)-2-propenyl]2-thienyl acetonitrile (II.3; R1 = 3-thienyl; R3 = R4 = CH3; R5 = 2-thienyl; Q = —CH=CH—)
Rdt = 85% (coarse) CCM: 0.50; S.C.
RMN: 2.35 (s, 6H); 2.9–3.2 (m, 2H); 5.7 (dt, 1H); 6.45 (d, 1H); 6.85–7.50 (m, 6H)

Example 2.wc: ā-dimethylamino-ā-[3-(3-thienyl)-2-propenyl]3-thienyl acetonitrile (II.3; R1 = 3-thienyl; R3 = R4 = CH3; R5 = 3-thienyl; Q = —CH=CH—)
Rdt = 75% (coarse) CCM: 0.75; S.C.
RMN: 2.30 (s, 6H); 2.9 (m, 2H); 5.6 (dt, 1H); 6.40 (d, 1H); 7.0–7.45 (m, 6H)

Example 3: ā-cinnamyl-ā-ethyl-benzylamine (I.1; R1 = R5 = C6H5; R2 = C2H5; R3 = R4 = H)

Add 58.0 g (0.209 mol) of the compound of example 1-a: ã-cinnamyl-ã-ethylbenzylisocyanate to a mixture of 1.5 l of tetrahydrafurane, 0.2 l of water and 50 ml of concentrated hydochloric acid (d=1.19). Heat the solution to reflux for 18 hours while stirring.

After cooling, eliminate the THF by distillation in vacuum and in a boiler. Add 200 ml of water to the residue, alkalinise the mixture cold until pH 10 by adding concentrated solution of sodium hydroxide then extract in three stages by 150 ml of ether. Collect the etherised phases, wash with water and then dehydrate on magnesium sulphate.

Eliminate the ether by distilllation, purify the orange coloured oily residue (54.8 g) by distillation in a vacuum. The product is obtained in the form of a viscous colourless oil. Eb/0.01 = 135°-150° C.

Weight = 38.0 g    Rdt = 72%    CCM: 0.15-0.20; S.C.

RMN: 0.70 (t, 3H); 1.45 (s, 2H scale D20); 1.80 (m, 2H); 2.60 (m, 2H); 6.00 (m, 1H); 6.45 (m, 1H); 7.10-7.55 (m, 10H).

Chlorohydrate:

To a solution of 13.04 g (53.3 mmol) of the product previously obtained in 100 ml of ether, add 20 ml of 2.8M hydrochloric ether at a temperature below 20° C.

Evaporate the solution and crystallise the white solid residue in an etherhexanes mixture.

Weight: 10.07 g    F = 85-110° C.    Rdt = 67%
Anal. (C18H21N.HCl) C.H.Cl.N

The benzylamines of examples 4 to 15 described below are obtained by the method of example 3 above starting from the isocyanate derivatives of formula (II-1) described in examples 1.b to 1.m.

Example 4: ã-cinnamyl-ã-ethyl-p.chlorobenzylamine
(I.1; R1 = p.Cl—C6H4; R2 = C2H5; R3 = R4 = H; R5 = C6H5; Q = —CH=CH—)
Starting from 1.b:
Rdt = 88% (coarse) CCM: 0.50-0.60; S.L.
RMN: 0.75 (t, 3H); 1.60 (s, 2H scale D20); 1.40-2.00 (m, 2H); 2.30-2.90 (m, 2H); 5.70-6.60 (m, 2H); 6.85-7.75 (m, 9H)
Chlorohydrate, monohydrate:
Rdt = 92% F = 100-110° C. (ethanol-water)
Anal. (C18H20ClN.HCl.H20) C,H,Cl,N Example 5: ã-cinnamyl-ã-ethyl-3,4 dichlorobenzylamine
(I.1; R1 = 3,4Cl2—C6H3; R2 = C2H5; R3 = R4 = H; R5 = C6H5; Q = —CH=CH—)
Starting from 1.c:
Rdt = 78% (coarse) CCM: 0.60-0.80; S.L.
RMN: 0.75 (t, 3H); 1.45 (s, 2H scale D20); 1.60-2.00 (m, 2H0; 2.30-2.85 (m, 2H); 5.70-6.55 (m, 2H); 7.15-7.65 (m, 8H)
Chlorohydrate:
Rdt = 85% F = 204-207° C. (methanol-ether)
Anal. (C18H19Cl2N.HCl) C.H.Cl,N Example 6: ã-cinnamyl-ã-ethyl-p.methylbenzylamine
(I.1; R1 = p.CH3—C6H4; R2 = C2H5; R3 = R4 = H; R5 = C6H5; Q = —CH=CH—)
Starting from 1.d:
Rdt = 22% Eb/0.1 = 145-150° C. CCM = 0.45-0.65; S.L.
RMN: 0.60 (t, 3H); 1.30-1.85 (m, 2H) 1.80 (s, 2H scale D20); 2.20 (m, 3H); 2.35 = 3.65 (m, 2H); 5.50-6.50 (m, 2H); 6.85— = 7.35 (m, 9H)
Anal. (C19H23N) C.H.N Example 7: ã-cinnamyl-ã-ethyl-(m.trifluoromethyl)benzylamine
(IK.1; R1 = m.F3C—C6H4; R2 = C2H5; R3 = R4 = H; R5 = C6H5; Q = —CH=CH—)
Starting from 1.e:
Rdt = 71% (coarse) CCM: 0.35-0.50; S.K.
RMN: 0.70 (t, 3H); 1.60 (s, 2H scale D20); 1.50-2.05 (m, 2H); 2.60-2.85 (m, 2H); 5.70-6.55 (m, 2H); 7.10-7.85 (m, 9H)
Chlorohydrate:
Rdt = 64% F = 208° C. (ether) ·
Anal. (C19H20F3N.HCl) C,H,Cl,F,N Example 8: ã-cinnamyl-ã-ethyl-p.metoxybenzylamine
(I.1; R1 - p.CH30—C6H4; R2 = C2H5; R3 = R4 = H; R5 = C6H5; Q = —CH=CH—)
Starting from 1.f.:
Rdt = 59% EB/0.1 = 160-165° C. CCM: 0.70-0.90; S.L.
RMN: 0.75 (t, 3H); 1.60 (s, 2H scale D20); 1.45-2.10 (m, 2H0; 2.50-2.75 (m, 2H); 5.65-6.65 (m, 2H); 6.80-7.55 (m, 9H)
Chlorohydrate:
Rdt = 87% F = 95-105° C. (petroleum ether)
Anal. (C19H23NO.HCl) C,H,Cl,N,O Example 9: ã-(3',4'-dichloro) cinnamyl-ã-methylbenzylamine
(I.1; R1 = C6H5; R2 = CH3; R3 = R4 = H; R5 = 3,4Cl2—C6H3; Q = —CH=CH—)
Starting from 1.g:
Rdt = 96% (coarse) CCM: 0.30-0.50; S.M.
RMN: 1.50 (t, 3H); 1.60 (s, 2H scale D20); 2.50-2.70 (M, 2H); 5.65-6.20 (m, 2H); 6.90-7.60 (m, 8H)

Chlorohydrate:
Rdt = 65% F = 209-210° C. (methanol-ether)
Anal. (C17H17Cl2N.HCl) C,H,Cl,N Example 10: ã-(3',4'-dichloro) cinnamyl-ã-ethyl-benzylamine (I.1; R1 = C6H5; R2 = C2H5; R3 = R4 = H; R5 = 3.4Cl2—C6H3; Q = —CH=CH—)
Starting from 1.h:
Rdt - 87% (coarse) CCM: 0.65-0.70; S.E.
RMN: 0.90 (t, 3H); 1.90-2.40 (m, 2H); 2.90-3.25 (m, 2H); 6.30 (s, 2H); 7.10-7.70 (m, 7H); 9.05-9.65 (m, 3H)
Chlorohydrate:
Rdt = 85% F = 165-170° C. (methanol-ether)
Anal. (C18H19Cl2N.HCl) C,H,Cl,N Example 11: ã-(3',4'-dichloro)cinnamyl-ã-isopropylbenzylamine (I.1; R1 = C6H5; R2 = (Ch3)2—CH; R3 = R4 = H; R5 = 3.4Cl2—C6H3; Q = —CH=CH—)
Starting from 1.i:
Rdt = 44% (chromatography) CCM: 0.25-0.45; S.K.
RMN: 0.70 (d, 3H); 1.00 (d, 3H); 1.70 (s, 2H scale D20); 1.85-2.90 (m, 1H); 3.45-3.70 (q, 2H); 5.60-6.40 (m, 2H); 6.85-7.50 (m, 8H)
Chlorohydrate:
Rdt = 87% F = 129° C. (ethanol-ether)
Anal. (C19H21Cl2N.HCl) C,H,Cl,N Example 12: ã-(3',4'-dichloro)cinnamyl-ã-ethyl-p.methylbenzylamine (I.1; R1 = p.CH3—C6H4; R2 = CH5; R3 = R4 = H; R5 - 3.4Cl2—C6H3; Q = —CH=CH—)
Starting from 1.j:
Rdt = 61% (chromatography) CCM: 0.70; S.M.
RMN: 0.70 (t, 3H); 1.50 (s, 2H scale D20); 1.55-2.05 (m, 2H); 2.30 (s, 3H); 2.35-2.85 (m, 2H); 5.70-6.45 (m, 2H); 6.95-7.40 (m, 7H)
Chlorohydrate:
Rdt = 85% F = 190° C. (methanol-ether)
Anal. (C19H21Cl2N.HCl) C,H,Cl,N Example 13: ã-(3',4'-dichloro)cinnamyl-ã-isopropylmetoxybenzylamine (I.1; R1 = p.CH3O—C6H4; R2 = CH5; R3 = R4 = H; R5 = 3.4Cl2—C6H3; Q = —CH=CH—)
Starting from 1.k:
Rdt = 92% (coarse) CCM: 0.40; S.L.
RMN: 0.75 (t, 3H); 1.50 (s, 2H scale D20); 1.60-2.00 (m, 2H); 2.25-2.85 (m, 2H); 3.80 (s, 3H); 5.70-6.40 (m, 2H); 6.75-7.40 (m, 7H)
Chlorohydrate:
Rdt = 92% F = 158° C. (ethyl acet.)
Anal. (C19H21Cl2NO.HCl) C,H,Cl,N,O Example 14: ã-(3'4'-dichloro)cinnamyl-ã-ethyl-p.chlorobenzylamine (I.1; R1 = p.Cl—C6H4; R2 = C2H5; R3 = R4 = H; R5 = 3,4Cl2—C6H3; Q = —CH=CH—)
Starting from 1.l:
Rdt = 76% (chromatography) CCM: 0.55; S.L.
RMN: 0.70 (t, 3H); 1.40-2.10 (m, 4H of which 2 scale D20); ; 2.40-2.85 (m, 2H); 5.70-6.50 (m, 2H); 6.90-7.65 (m, 7H)
Chlorohydrate:
Rdt = 87% F = 166° C. (ether)
Anal. (C18H18Cl3N.HCl) C,H,Cl,N Example 15: ã-(3',4'-dichloro)cinnamyl-ã-ethyl-m.trifluoromethylbenzylamine (I.1; R1 = mF3C—C6H4; R2 = C2H5; R3 = R4 = H; R5 = 3.4Cl2—C6H3; Q = —CH=CH—)
Starting from 1.m:
Rdt = 96% (coarse) CCM: 0.75; S.L.
RMN: 0.75 (t, 3H); 1.30-2.10 (m, 4H of which 2 scale D20); 2.40-2.90 (m, 2H); 5.70-6.40 (m, 2H); 6.90-7.805 (m, 7H)
Chlorohydrate:
Rdt = 83% F = 255° C. (methylene chloride)
Anal. (C19H18Cl2F3N.HCl) C,H,Cl,F,N Example 16:

A - (−) tartrate of (+) ã-cinnamyl-ã-ethyl-benzylamine
(I.1: R1 = R5 = C6H5; R2 = C2H5; R3 = R4 = H; Q = —CH=CH—)

4.0 liters of demineralised water is introduced in a 6 liter reactor which is heated to reflux while being stirred. Then 213.0 g (0.487 mol) of ã-cinnamyl-ã-ethyl-benzylamine (product of example 3) is added then 139.8 g (0.932 mol) of tartaric acid (−). The mixture is kept at reflux for 30 minutes then filtered hot on Buchner.

The solution which is slightly cloudy is left overnight to crystallise. The precipitate formed is filtered and dried in a vacuum at 60° C. until the weight is constant. 120.0 g of product is obtained. The filtrate is kept for processing. The product is recrystallised in 1.3 l of demineralised water at reflux. After allowing to stand overnight, the precipitate is filtered then dried in a vacuum. 115.7 g of product is obtained. The second filtrate is also kept.

It is recrystallised in the same way as previously: 92.4 g of product is obtained (0.230 mol). The third filtrate is also kept.

Optical purity of the products:

Samples of the purified insoluble substance and of the second and third crystallisation filtrate are treated with a sodium hydroxide solution then extracted with ether. The specific rotatory power of the residues is determined by polarimetry after evaporating the ether.

Results.

Residue of the filtrate of the second crystallisation
$[\bar{a}]_D^{25} = +12.3°$ (c=6.33; MeOH)
Residue of the filtrate of the third crystallisation
$[\bar{a}]_D^{25} = +36.9°$ (c=6.40; MeOH)
Residue of the precipitate of the third crystallisation
$[\bar{a}]_D^{25} = +40.0°$ (c=6.26; MeOH)

The precipitate obtained after the third crystallisation is considered of satisfactory optical purity:

| Weight = 92.4 g | F = 158° C. | Rdt = 54.3% |
| --- | --- | --- |

Anal. C18H21N, C4H6O4) C,H,N,O
$[\bar{a}]_D^{25}$ (base) = +40.0° C. (c=6.26; MeOH)
RMN (base): 0.70 (t,3H; 1.45 (s,2H scale D2O); 1.80 (m,2H); 2.60 (m,2H); 6.00 (m,1H); 6.45 (m,1H); 7.10–7.55 (m,10H)

B - (+) tartrate of (−)ā-cinnamyl-ā-ethyl benzylamine (I.1: R1 - R5 - C6H5; R2=C2H5; R3=R4=H; Q=—CH=CH—)

The filtrate obtained from the first crystallisation of product A is alkalinised by a concentrated solution of sodium hydroxide and extracted by 3 times 500 ml of ether. The collected etherised phases are washed by a saturated solution of sodium chloride then dehydrated on Na2SO4. The ether is eliminated by distillation.

Weight of the residue: 135.0 g
$[\bar{a}]_D^{25} = -20.6°$ (c=5.7; MeOH)

The product is introduced at reflux in 2.3 l of water and 88.7 g (0.59 mol) of tartaric acid (D-(+) is added. The solution is left overnight after dissolving and filtering to eliminate the mechanical impurities.

The precipitate formed is filtered and dried at 60° C. in a vacuum. Weight: 149.0 g. The filtrate from the first crystallisation is kept.

The insoluble substance is recrystallised in 1.5 l of water at the reflux; the precipitate is filtered and dried after leaving overnight. Weight: 127.0 g. The filtrate is kept.

Optical purity of the product.

Proceed in the same way as described for A with a specimen of the filtrates from the first and second crystallisations as well as with the product obtained after the second crystallisation.

Results.
Filtrate of the first crystallisation
$[\bar{a}]_D^{25} = +18.0°$ (c=6.30; MeOH)
Filtrate of the second crystallisation
$[\bar{a}]_D^{25} = -23.0°$ (c=6.10; MeOH)
Precipitate of the second crystallisation
$[\bar{a}]_D^{25} = -39.3°$ (c=5.5; MeOH)

This latter product is considered to have satisfactory optical purity and comparable with that of the product A obtained previously.

| Weight: 127.0 g | F = 158° C. | Rdt = 74.7% |
| --- | --- | --- |

Anal. (C18H21N, C4H6O4) C,H,N,O
$[\bar{a}]_D^{25}$ (base) = −39.3° (c=5.5; MeOH)
RMN (base) : 0.70 (t,3H); 1.45 (s, 2H D2O scale); 1.80 (m,2H); 2.60 (m,2H); 6.00 (m,1H); 6.45 (m,1H); 7.10–7.55 (m,10H)

Example 17

A (+) ā-cinnamyl-ā-ethyl-p.chlorobenzylamine (I.1; R1=p.C1-C6H4; R2=C2H5; R3=R4=H; R5=C6H5; Q=—CH=CH—)

Isolate the (−) enantiomer dextrogyre tartrate as described in example 16 above and starting from the racemic a-cinnamyl-a-ethyl-p.fluorobenzylamine of example 4 and the (−) tartaric acid, which when treated in an alkaline atmosphere and extracted with dichloromethane will enable the product to be obtained in the basic form.

| Rdt = 60% | CCM: 0.5; S.L. |
| --- | --- |

$[\bar{a}]_D^{20} = +66.4$ (c=6.0; MeOH)
RMN: 0.75 (t,3H); 1.60 (s,2H D2O scale); 1.40–2.00 (m,2H); 2.30–2.90 (m,2H); 5.70–6.60 (m,2H); 6.85–7.75 (m,9H)
Chlorohydrate:

| Rdt = 83% | F = 204–205° C. (ether) |
| --- | --- |

$[\bar{a}]_D^{20} = +25.4°$ C. (c=5.0; MeOH)
Anal. (C19H2OClN,HCl) C,H,Cl,N

B - (−)ā-cinnamyl-ā-ethyl-p.chlorobenzylamine (I.1; R1=p.C1-C6H4; R2=C2H5; R3=R4=H; R5=C6H5; Q=—CH=CH—)

The compound is obtained by treating the above filtrate of the enantiomer (+) crystallisation then preparing diastereo isomers with the (+) tartaric acid and purifying by crystallisation in the same way as in example 16B. The compound is finally obtained in its free basic form.

| Rdt = 47% | CCM: 0.5; S.L. |
| --- | --- |

$[\bar{a}]_D^{20} = 0\ 64.2°$ (c=6.2; MeOH)
RMN: 0.75 (t,3H); 1.60 (s,2H D2O scale); 1.40–2.00 (m,2H); 2.30–2.90 (m,2H); 5.70–6.60 (m,2H); 6.85–7.75 (m,9H)
Chlorohydrate:

| Rdt = 77% | F = 202–204° C. (ether) |
| --- | --- |

$[\bar{a}]_D^{20} = -23.6°$ (c=5.2; MeOH)
Anal. (C18H2OClN,HCl) C,H,Cl,N

Example 18

ā-cinnamyl-ā-ether-N-methyl-benzylamine (I.2: RF1=R5=C6H5; R2=C2H5; R3=CH3; R4=H; Q=—CH=CH—)

145.0 g (1.09 mol) of aluminum chloride is introduced in a nitrogen atmosphere in a 12 l reactor cooled in an ice bath. 900 ml of anhydrous THF is added gently and with precaution. 3.2 l of M lithium aluminum hydride solution (3.2 mol) in the THF is added to the reddish solution obtained. The mixture is stirred for 15 minutes the 233.0 g (0.84 mol) of ā-cinnamyl-ā-ethylbenzylisocyanate (example 1.a) in solution in 200 ml of THF is added drop by drop without exceeding 5° C.

After its introduction the mixture is kept stirred for 4 hours at the laboratory temperature then cooled to approximately 5° C. by an ice bath.

1.8 l methyl-t.butylic ether is added then 195 ml of NaOH solution at 10% (w/v) is added droop by drop carefully. Then 240 ml of water is added and the mixture stirred for 16 hours at ambient temperature.

The suspension is filtered on Buchner and in a vacuum. The insoluble substance is separated and the filtrate concentrated by distillation in a vacuum and in a boiler. The residual coarse product is viscous yellow oil which is purified by distillation. Purified product: Eb/0.02=135°-150° C., which crystallises in the hexane.

| Weight = 183.2 g | F = 54–56° C. | Rdt = 82% |
|---|---|---|

CCM: 0.45–0.55; S.C.
Anal. (C19H23N) C,H,N
RMN: 0.70 (t,3H); 1.40 (s,1H scale D2O); 1.80 (q,2H); 2.20 (s,3H); 2.70 (d,2H); 6.00–6.45 (m,2H); 7.10–7.60 (m,10H)

The reduction of the isocyanates of the examples 1-b, 1-c, 1-e, 1-f and 1-i to 1-m will lead to the compounds of the invention described in the examples 19 to 27 as applied in the previous example.

Example ~ ..nan.,..-..nyl-N-methyl-p.chlorobenzylamine
(I.2; R1 = p.Cl-C6H4; R2 = C2H5; R3 = CH3; R4 = H; R5 = C6H5; Q = —CH=CH—)
    Rdt = 74%    F = 50° C. (hexanes)    CCM: 0.40–0.70; S.L.
RMN: 0.75 (t,3H); 1.40–1.90 (m,3H of which 1H scale); 2.15 (s,3H); 2.60 (d,2H); 5.70–6.50 (m,2H); 7.10–7.45 (m,9H)
Chlorohydrate:
    Rdt = 82%    F = 205–210° C. (methanol)
Anal. (C19H22ClN.HCl) C,H,Cl,N Example ~ ..inan ~ ..yl-N-methyl-3,4-dichlorobenzylamine
(I.2; R1 = 3,4Cl2-C6H3; R2 = C2H5; R3 = CH3; R4 = H; R5 = C6H5; Q = —CH=CH—)
    Rdt = 59%    F = 68° C. (hexanes)    CCM: 0.50–0.70; S.L.
RMN: 0.75 (t,3H); 1.35 (s,1H scale); 1.75 (q,2H); 2.15 (s,3H); 2.65 (d,2H); 5.80–6.55 (m,2H); 7.10–7.70 (m,8H)
Chlorohydrate:
    Rdt = 75%    F = 206–208° C. (methanol)
Anal. (C19H21Cl2N.HCl) C,H,Cl,N Example 2 ~ nan ~ yl-N-methyl-(m.trifluoromethyl)benzylamine
(I.2; R1 = m.F3C-C6H4; R2 = C2H5; R3 = CH3; R4 = H; R5 = C6H5; Q = —CH=CH—)
    Rdt = 93% (coarse)    CCM: 0.80–0.90; S.L.
RMN: 0.70 (t,3H); 1.50 (s,1H scale); 1.80 (q,2H); 2.20 (s,3H); 2.65 (d,2H); 5.70–6.55 5m, 2H); 7.10–7.80 (m,9H)
Chlorohydrate:
    Rdt = 68%    F = 172° C. (ethanol)
Anal. (C20H22F3N.HCl) C,H,Cl,F,N Example 2 ~ inan ~ yl-N-methyl-p.methoxybenzylamine
(I.2; R1 = p.CH3O-C6H4; R2 = C2H5; R3 = CH3; R4 = H; R5 = C6H5; Q = —CH=CH—)
    Rdt = 52% (chromatography)    F = 95°    CCM: 0.40–0.60; S.M.
Anal. (C20H25NO) C,H,N,O
RMN: 0.75 (t,3H); 1.55 (s,1H scale); 1.80 (q,2H); 2.20 (s,3H); 2.65 (d,2H); 3.85 (s,3H); 5.75 ′ :° (m,2H); 6.60–7.60 (~ °H)

Example 2 ~ ,4′-dichloro)cinnam ~ ipropyl-N-methyl-benzylamine
(I.2; R1 = conj; R2 = (CH3)2=CH; R3 = CH3; R4 = H; R5 = 3,4Cl2-C6H3; Q = —CH=CH—)
    Rdt = 54% (chromatography)    CCM: 0.50–0.70; S.L.
RMN: 0.70 (d,3H); 0.80 (d,3H); 1.40 (s,1H scale); 1.90 (q,1H); 2.30 (s,3H); 2.80–3.00 (m,2H); 6.00–6.60 (m,2H); 7.05–7.50 (m,8H)
Chlorohydrate:
    Rdt = 79%    F = 156–160° C. (ether)
Anal. (C20H23Cl2N.HCl) C,H,Cl,N Example ~ ,4′-dichloro)cinnan ~ l-N-methyl-p.methylbenzylamine
(I.2; R1 = CH3-C6H4; R2 = C2H5; R3 = CH3; R4 = H; R5 = 3,4Cl2-C6H3; Q = —CH=CH—)
    Rdt = 45% (chromatography)    CCM: 0.60; S.K.
RMN: 0.70 (t,3H); 1.60–2.05 (m,2H); 2.20 (s,4H of which 1 scale D20); 2.30 (s,3H); 2.70 (d,2H); 5.70–6.45 (m,2H); 7.00–7.50 (m,7H)
Chlorohydrate:
    Rdt = 87%    F = 196° C. (methanol-ether)
Anal. (C20H23Cl2N.HCl) C,H,Cl,N Example 25 ~ 4′-dichloro)cinnam ~ yl-N-methyl-p.methoxybenzylamine
(I.2; R1 = p.CH3O-C6H4; R2 = C2H5; R3 = CH3; R4 = H; R5 = 3,4Cl2-C6H3; Q = —CH=CH—)
    Rdt = 40% (chromatography)    CCM: 0.55; S.L.
RMN: 0.70 (t,3H); 1.40 (s,1H scale D20); 1.60–1.90 (q,2H); 2.15 (s,3H); 2.60 (d,2H); 3.80 (s,3H); 5.70–6.40 (m,2H); 6.70–7.40 (m,7H)
Chlorohydrate:
    Rdt = 77%    F = 186° C. (ethyl acetate)
Anal. (C20H23Cl2NO.HCl) C,H,Cl,N Example . ~ ′-dichloro)cinnamy ~ hyl-N-methyl-p.chlorobenzylamine
(I.2; R1 = p.Cl-C6N4; R2 = C2H5; R3 = CH3; R4 = H; R5 = 3,4Cl2-C6H3; Q = —CH=CH—)
    Rdt = 86% (coarse)    CCM: 0.50; S.L.
RMN: 0.70 (t,3H); 1.35 (s,1H scale D20); 1.80 (q,2H); 2.20 (s,3H); 2.65 (d,2H);

-continued 5.70-6.50 (m,2H); 6.90-7.50 (m,7H)
Chlorohydrate:
Rdt = 79%   F = 180° C. (methanol-ether)
Anal. (C1?H??C'3N.HCl) C,H,Cl,N
Example    4'-dichloro)cinnamyl-a-ethyl-N-methyl-
m.trifluoromethylbenzylamine
(I.2; R1 = m.F3C-C6H4; R2 = C2H5; R3 = CH3; R4 = H; R5 = 3,4C12-C6H3; Q = —CH=CH—)
Rdt = 88% (coarse)   CCM: 0.70; S.L.
RMN: 0.75 (t,3H); 1.40 (s,1H scale D2O); 1.85 (q,2H); 2.20 (s,3H); 2.70 (d,2H); 5.70-6.45 (m,2H); 6.95-7.85 (m,7H)
Chlorohydrate:
Rdt = 93%   F = 165° C. (ether)
Anal. (C20H??C'?F3N !!C': C,H,Cl,F,N
Example 28 " inar " hyl-N-methyl benzylamine
(I.2; R1 = R5 = C6H5; R2 = C2H5; R3 = CH3; R4 = H; Q = —CH=CH—)

Example 28

(—) ã-cinnamyl-ã-ethyl-N-methyl benzylamine (I.2; R1=R5=C6H5; R2=C2H5; R3=CH3; R4=H; Q=—CH=CH—)

182 ml of anhydrous THF, 7.7 g (0.167 mol) of pure formic acid and 26.6 g (0.164 mol) of 1,1'-carbonyl-diimidazol is introduced in a reactor protected from humidity and under a nitrogen atmosphere.

The solution is stirred for one hour at ambient temperature then 40.0 g (0.159 mol) of (+) ã-cinnamyl-ã-ethyl-benzylamine obtained as in example 16A in solution in 430 ml of anhydrous THF added.

It is introduced in 15 minutes at ambient temperature and stirring is maintained for 4 hours.

The THF is eliminated by distillation in a vacuum and in a boiler and the residue recovered by 300 ml of N. HCl solution. The mixture is extracted with ether and the acid phase separated. The etherised phase is extracted by a saturated sodium bicarbonate solution then with water and finally dehydrated on Na2SO4. The ether is concentrated until a residual volume of 200 ml is obtained. This residual etherised solution is kept at 4° C. for 24 hours.

The insoluble crystalline substance precipitated is (+) ã-cinnamyl-ã-ethyl-N-formyl-benzylamine (intermediary II.2 of formula II.2.1; R1=R5=C6H5; R2=C2H5; R6=H; Q=—CH=CH—.

It is filtered, dried in a vacuum at 60° C. until the weight remains constant.

Weight: 41.0 g   F = 101° C.   Rdt = 92.3%

$[\tilde{a}]_D^{25} = +38.5°$ (c=4.05; MeOH)

25.5 g (0.192 mol) of aluminum chloride is introduced into a reactor protected from humidity and in a nitrogen atmosphere. The reactor is cooled by a carbonic ice/acetone bath and 309 ml of anhydrous ether is added in 15 minutes approximately and without exceeding 0° C. A solution is obtained which is kept at 0° C. for 30 minutes.

Simultaneously, 22.3 g (0.587 mol) of aluminum lithium hydride is introduced in a reactor also protected from humidity and in a nitrogen atmosphere and after cooling by a carbonic ice/acetone bath, 309 ml of anhydrous THF added in 10 minutes approximately.

The suspension obtained is kept stirred for 15 minutes at 0° C. then transferred to the first reactor containing the etherised aluminum chloride solution. The transfer is carried out in 10 minutes at a temperature below 0° C.

After stirring for 30 minutes, add 41.0 g (0.147 mol) of the previous intermediate agent in solution in 120 ml of anhydrous THF in 30 minutes and at a temperature of approximately 0° C.

After returning to 20° C., the reactive mixture is raised to reflux while stirring for 2 hours.

Recool to 0° C. then introduce drop by drop 47.8 ml of a sodium hydroxide solution at 10% (w/v) then 42 ml of water.

The mixture is left overnight, the insoluble substance filtered on Buchner and washed with the THF. The filtrates collected are evaporated in a vacuum and in a boiler. A coarse oily residue is obtained.

Weight: 36.1 g
$[\tilde{a}]_D^{25} = -12.4°$ (c=6.39; MeOH)

The product is purified by chromatography in a silicon column. The purified product can be obtained in the form of a colourless oil by the elution by a 98-2 (v/v) mixture of methylene-methanol chloride.

Weight: 32.6 g   Rdt = 83.5%   CCM: 0.45-0.55; S.L.

$[\tilde{a}]_D^{25} = -16.4°$ (c=6.1; MeOH)
RMN (base): 0.70 (t,3H); 1.40 (s,1H scale D2O); 1.80 (q,2H); 2.20 (s,3H); 2.70 (d,2H); 5.75-6.50 (m,2H); 7.10-7.60 (m,10H)

(+) Dehydrated tartrate:

32.6 g (0.123 mol) of the previous product is dissolved in 250 ml of ethanol at 95% in a reactor equipped in reflux position.

Simultaneously, 20.3 g (0.135 mol) of tartaric acid D-(+) is dissolved at reflux in 250 ml of ethanol at 95%.

This hot solution is introduced into the solution of the product. The mixture is stirred for 15 minutes at the reflux then left one night at ambient temperature. The insoluble substance is filtered then dried at 60° C. in a vacuum.

Weight: 51.0 g   F = 127° C.   Rdt = 91.8%

Anal. (C19H23N, C4H6O6, 2H2O) C,H,N,O

Example 29

(+) ã-cinnamyl-ã-ethyl-N-methyl benzylamine (I.2; R1=R5=C6H5; R2=C2H5; R3=CH3; R4=H; Q=—CH=CH—).

The following is obtained by proceeding in the same manner as that described for example 28 and starting with 40.0 g of (−) a-cinnamyl-a-ethyl-benzylamine prepared as in example 16B:

(−)ā-cinnamyl-ā-ethyl-N-formyl benzylamine
(Agent II.2.1 - R1=R5=C6H5; R2=C2H5; R6=H; Q=—CH=CH—)

| Weight: 39.3 g | F = 101° C. | Rdt = 88.5% |

$[\tilde{a}]_D^{25} = -37.9°$ (c=5.82; MeOH)

Then after reducing 39.0 g (0.140 mol) of this compound and as described in example 28, 36.4 g of the following product is obtained in the coarse state as described in example 28:

$[\tilde{a}]_D^{25} = +15.3°$ (c=5.1; MeOH)

which is purified by chromatography on a silicon column.

| Weight: 31.3 g | Rdt = 84.2% | CCM: 0.45-0.55; S.L. |

$[\tilde{a}]_D^{25} = +16.3°$ (c=5.58; MeOH)
RMN: 0.70 (t,3H); 1.40 (s,1H scale D2O); 1.80 (q,2H); 2.20 (s,3H); 2.70 (d,2H); 5.75-6.50 (m,2H); 7.10-7.60 (m,10H)

(−) Dehydrated tartrate:

The purified product is obtained by preparing by salination of 15.5 g (0.058 mol) of the product with 9.64 g (0.064 mol) of tartaric acid 1(−).

| Weight: 25.2 g | F = 128° C. | Rdt = 96.2% |

Anal. (C19H23N, C4H6O6, 2H2O) C,H,N,O

Example 30

ā-cinnamyl-N,N-dimethyl-ā-ethyl-benzylamine (I.3; R1=R5=C6H5; R2=C2H5; R3=R4=CH3; Q=—CH=CH—)

2.8 l of solution of 2.0M ethylmagnesium bromide (5.6 mol) in the THF is introduced in a reactor protected from humidity and in a nitrogen atmosphere.

340.0 g (124 mol) of ā-dimethylamino-ā-cinnamyl-phenylacetonitrile (example 2-a) in solution and 2 l of THF is introduced in 15 minutes, while stirring and at ambient temperature.

The mixture is stirred at laboratory temperature for 3 hours then 5.5 l of saturated aqueous ammonium chloride solution is added carefully without exceeding 20° C.

The aqueous phase is decanted and extracted by 2×800 ml of a mixture of hexanes-ethyl acetate 1-3 (v/v).

The collected organic phases are extracted by 2×730 ml of N HCl solution. The collected aqueous acid phases are alkylinised by a concentrated sodium hydroxide solution then the mixture extracted by 3×800 ml of hexane-ethyl acetate mixture. The collected organic phases are washed with water, dried on MgSO4 then evaporated in a vacuum. The yellow residual oil (282.0 g) is purified by crystallisation in the hexane.

| Weight = 166.1 g | Rdt = 48% | F = 60-65° C. |

CCM: 0.35-0.45; S.C.
RMN: 0.80 (t,3H); 1.90 (q,2H); 2.25 (s,6H); 2.90 (d,2H); 6.00-6.60 (m,2H); 7.10-7.55 (m,10H)

Chlorohydrate:
72.4 g (0.229 mol) of the previous product is dissolved in 400 ml of ether.

140 ml of 2N hydrochloric ether (0.280 mol) solution is added to this solution. Methanol is added to dissolve the sticky solid formed and the solution is left for 3 days at 4° C. The white precipitate is filtered and dried in a vacuum.

| Weight = 64.5 g | Rdt = 79% | F = 182-184° C. |

Anal. (C20H25N.HCl) C,H,Cl,N

The products of examples 31-46 which follow are obtained by the previous method of operation using ā-dimethylamino phenylacetonitriles of examples 2 to react with the suitable organic magnesium halogenides.

---

Example ā-cinnamyl-N,N-dimethyl-ā-ethyl-p.chlorobenzylamine (I.3; R1 = p.Cl-|C6H4; R2 = C2H5; R3 = R4 = CH3; R5 = C6H5; Q = —CH=CH—)
Starting from 2.b and C2H5MgBr
Rdt = 49%          F = 45-50° C. (ethanol)
CCM: 0.40-0.60; S.K.
RMN: 0.75 (t,3H); 1.85 (q,2H); 2.25 (s,6H); 2.80 (d,2H); 5.95-6.55 (m,2H); 7.10-7.45 (m,9H)
Chlorohydrate:
Rdt = 58%          F = 204° C. (ethanol)
Anal. (C20H27 .. 1N.HCl) C,H,Cl,N Example ā-cinnamyl-N,N-dimethyl-ā-ethyl-(3,4-dichloro)benzylamine (I.3; R1 = 3,4C12-C6H3; R2 = C2H5; R3 = R4 = CH3; R5 = C6H5; Q = —CH=CH—)
Starting with 2.c and C2H5MgBr:
Rdt = 54%          F = 82° C. (petroleum ether)
CCM: 0.85-0.95; S.K.
RMN: 0.75 (t,3H); 1.85 (q,2H); 2.25 (s,6H); 2.80 (d,2H); 5.95-6.55 (m,2H); 7.10-7.60 (m,8H)
Chlorohydrate:
Rdt = 72%          F = 215° C. (methanol)
Anal. (C20H .. 12N.HCl) C,H,Cl,N Example ā-cinnamyl-N,N-dimethyl-ā-ethyl-p.trifluoromethylbenzylamine (I.3; R1 = p.CH3-C6H4; R2 = C2H5; R3 = R4 = CH3; R5 = C6H5; Q = —CH=CH—)
Starting from 2.d and C2H5MgBr
Rdt = 51% (chromatography)  · CCM: 0.75-0.85; S.N.
RMN: 0.80 (t,3H); 1.95 (q,2H); 2.25 (s,6H); 2.35 (s,3H); 2.90 (d,2H); 6.00-6.65 (m,2H); 7.05-7.45 (m,9H)
Chlorohydrate:

-continued

Rdt = 83%                F = 197° C. (methanol-ether)
Anal. (C2̲ ̲ ̲ ̲ ̲ ̲HCl) C,H,Cl,N
Example ̲ ̲. ̲ ̲ ̲namyl-N,N-dimeth̲ ̲ ̲ ̲yl-p.trifluoromethylbenzylamine (I.3; R1 = p.F3C-C6H4; R2 = C2H5; R3 = R4 CH3; R5 C6H5; Q = —CH=CH—)
Starting from 2.e and C2H5MgBr
Rdt = 33%                F = 52.C (ethanol)              CCM: 0.75-0.85; S.K.
RMN: 0.75 (t,3H); 1.90 (q,2H); 2.30 (s,6H); 2.85 (d,2H); 6.00-6.60 (m,2H): 7.15-
7.40 (m,5H); 7.60 (s,4H)
Chlorohydrate:
Rdt = 76%                F = 196-198° C. (petroleum ether)
Anal. (C21H24F̲ ̲N.HCl) C,H,Cl,F,N̲
Example 3_ ̲ namyl-N,N-dimetl ̲ hyl-p.methoxybenzylamine (I.3; R1 = p.CH3O-C6H4; R2 = C2H5; R3 = R4 = CH3; R5 = C6H5; Q = —CH=CH—)
Starting from 2.f and C2H5MgBr
Rdt = 47%                F = 55° C. (hexanes)            CCM: 0.20-0.40; S.L.
RMN: 0.80 (t,3H); 1.90 (q,2H); 2.25 (s,6H); 2.85 (d,2H); 3.80 (s,3H): 6.00-6.60
(m,2H); 6.80-7.45 (m,9H)
Chlorohydrate:
Rdt = 77%                F = 167° C. (methanol)
Anal. (C2̲ ̲H̲ ̲ ̲O.HCl) C,H,Cl,N
Example ̲ ̲ ,4'-dichloro)cinnamyl-N,N-dimetl ̲ hyl-benzylamine (I.3; R1 = C6H5; R2 = C2H5; R3 = R4 = CH3; R5 = 3,4Cl2-C6H3; Q = —CH=CH—)
Starting from 2.gb and C2H5MgBr
Rdt = 58%                F = 76-80° C. (hexanes)          CCM: 0.30-0.40; S.B.
Anal. (C20H23Cl2N) C,H,Cl,N
RMN: 0.75 (t,3H); 1.80 (q,2H); 2.25 (s,6H); 2.85 (d,2H); 6.05-6.50 (m,2H); 7.05-
7.55 (m,8H)
Example 37: N,N-dimetl ̲ ̲ ̲ 4',5'-trimethoxylcinnamyl-benzylamine (I.3; R1 = C6H5; R2 = C2H5; R3 = R4 = CH3; R5 = 3,4,5(CH3O)3-C6H2; Q =
—CH=CH—)
Starting from 2.m and C2H5MgBr
Rdt 45%                  F = 116-118° C. (methanol)
CCM: 0.35 = 0.45; S.C.
Anal. (C23H31NO3) C,H,N,O
RMN: 0.80 (t,3H); 1.95 (q,2H); 2.25 (s,6H); 2.75-3.05 (m,2H); 3.90 (s,9H); 6.10-
6.45 (m,2H); 6.60 (s,2H); 7.20-7.70 (m,5H)
Example 38: N-allyl-ã-cinnamyl-ã-ethyl-N-methylbenzylamine (I.3; R1 = R5 = C6H5; R2 = C2H5; R3 = CH3; R4 = CH2—CH=CH2; Q = —CH=CH—)
Starting from 2.n and C2H5MgBr
Rdt = 45%                Eb/0.025 = 150-165° C.
CCM: 0.15-0.25; S.D.
Anal. (C22H27N) C,H,N
RMN: 0.75 (t,3H); 1.90 (q,2H); 2.35 (s,3H); 2.85 (d,2H); 3.10 (d,2H); 4.95-6.60
(m,5H); 7.10-7.60 (m,10H)
Example 39: N-allyl-ã-(3',4'dichloro)cinnamyl-ã-ethyl-N-methylbenzylamine (I.3; R1 = C6H5; R2 = C2H5; R3 = CH3; R4 = CH2—CH=CH2; R5 = 3,4Cl2-C6H3; Q =
—CH=CH—)
Starting from 2.o and C2H5MgBr
Rdt = 23%                Eb/0.5 = 190° C.                CCM: 0.45-0.55; S.A.
RMN: 0.75 (t,3H); 1.90 (q,2H); 2.30 (s,3H); 2.85 (d,2H); 3.05 (d,2H); 4.90-6.30
(m,5H); 7.00-7.60 (m,8H)
Chlorohydrate:
Rdt = 93%                F = 70-80° C. (methylene chloride)
Anal. (C22H25Cl2N.HCl) C,H,Cl,N
Example 40: ã-cinnamyl-N,N-dimethyl-ã-methyl-benzylamine (I.3; R1 = C6H5; R2 = CH3; R3 = R4 = CH3; R5 = C6Hr; Q = —CH=CH—)
Starting from 2.a and CH3MgBr
Rdt = 75% (coarse)       CCM: 0.50-0.65; S.M.
RMN: 1.30 (s,3H); 2.15 (s,6H); 2.30-2.85 (m,2H); 5.50-6.40 (m,2H); 7.00-7.50
(m,10H)
Example 41: ã-cinnamyl-N,N-dimethyl-ã-isopropylbenzylamine (I.3; R1 = C6H5; R2 = (CH3)2CH; R3 = R4 = CH3; R5 = C6H5; Q = —CH=CH—)
Starting from 2.a and (CH3)2CHMgBr
Rdt = 31%                F approx. 50° C. (ethanol)       CCM: 0.60; S.A.
RMN: 0.75 (m,6H); 2.40 (s,7H); 2.85-3.25 (m,2H); 6.20-6.60 (m,2H); 7.00-7.60
(m,10H)
Chlorohydrate:
Rdt = 92%                F = 134° C. (ethyl acetate)
Anal. (C21H27N.HCl) C,H,Cl,N
Example 42: ã-cinnamyl-N,N-dimethyl-ã-pentyl-benzylamine (I.3; R1 = C6H5; R2 = CH3-(CH2)4; R3 = R4 = CH3; R5 = C6H5; Q = —CH=CH—)
Starting from 2.a and CH3(CH2)4MgBr
Rdt = 25% (chromatography)   CCM: 0.80; S.M.
RMN: 0.70-1.00 (m,3H); 1.00-1.50 (m,6H); 1.70-2.00 (m,2H); 2.25 (s,6H); 2.85
(d,2H); 6.00-6.60 (m,2H); 7.00-7.50 (m,10H).
Example 43: ã-(3',4' dichloro) cinnamyl-N,N-dimethyl-ã-ethyl-
p.chlorobenzylamine
(I.3; R1 = p.Cl-C6H4; R2 = C2H5; R3 = R4 = CH3; R5 = 3,4Cl2-C6H3; Q = —CH=CH—)
Starting from 2.p and C2H5MgBr
Rdt = 50% (purified)     F = 66° C. (ethanol)            CCM: 0.80; S.A.

-continued

RMN: 0.60–0.90 (t,3H); 1.65–2.10 (q,2H); 2.25 (s,6H); 2.80 (d,2H); 6.00–6.50 (m,2H); 7.00–7.50 (m,7H)
Chlorohydrate:
Rdt = 96%                F = 134° C. (methanol)
Anal. (C20H22Cl3N.HCl) C,H,Cl,N Example 44: ã-(3',4'-dichloro) cinnamyl-N,N-dimethyl-ã-ethyl-p.methylbenzylamine (I.3; R1 = p.CH3-C6H4; R2 = C2H5; R3 = R4 = CH3; R5 = 3,4Cl2-C6H3; Q = —CH=CH—)
Starting from 2.q and C2H5MgBr
Rdt = 23% (purified)      F = 70° C. (ethanol)      CCM: 0.85; S.M.
RMN: 0.80 (t,3H); 1.60–2.10 (m,2H); 2.20 (s,6H); 2.35 (s,3H); 2.65–3.05 (m,2H); 6.00–6.50 (m,2H); 7.00–7.50 (m,7H)
Chlorohydrate:
Rdt = 87%                F = 138° C. (methanol)
Anal. (C21H25Cl2N.HCl) C,H,Cl,N Example 45: ã-(3',4'-dichloro) cinnamyl-N,N-dimethyl-ã-ethyl-p.trifluoromethylbenzylamine (I.3; R1 = F3C-C6H4; R2 = C2H5; R3 = R4 = CH3; R5 = 3,4Cl2=C6H3; Q = —CH=CH—)
Starting from 2.r and C2H5MgBr
Rdt = 24% (purified)      F = 66° C. (ethanol)      CCM: 0.20; S.G.
RMN: 0.75 (t,3H); 1.80–2.25 (m,2H); 2.35 (s,6H); 2.65–3.20 (m,2H); 5.90–6.50 (m,2H); 7.00–7.90 (m,7H).
Chlorohydrate:
Rdt = 85%                F = 150° C. (ethyl acetate)
Anal. (C21H22Cl2F3N.HCl) C,H,Cl,F,N Example 46: ã-(3',4'-dichloro)cinnamyl-N,N-dimethyl-ã-ethyl-p.metoxybenzylamine (I.3; R1 = p.CH3O-C6H4; R2 = C2H5; R3 = R4 = CH3; R5 = 3,4Cl2-C6H3; Q = —CH=CH—)
Starting from 2.s and C2H5MgBr
Rdt = 31% (purified)      F = 90° C. (ethanol)      CCM: 0.55; S.M.
RMN: 0.80 (t,3H); 1.90 (q,2H); 2.20 (s,6H); 2.80 (d,2H); 3.80 (s,3H); 6.10–6.50 (m,2H); 6.80–7.50 (m,7H)
Chlorohydrate:
Rdt = 90%                F = 210° C. (methanol)
Anal. (C21H25Cl2NO.HCl) C,H,Cl,N,O

Example 47

ã-cinnamyl-ã-ethyl-N-methyl-N-propylbenzylamine (I.3; R1=R5=C6H5; R2=C2H5; R3=CH3; R4=C3H7; Q=—CH=CH—)

a) 15.0 g (57 mmol) of ã-cinnamyl-ã-ethyl-N-methylbenzylamine (compound of example 18) is dissolved in 225 ml of dichloromethane in an anhydrous atmosphere. After adding 6.9 g (68 mmol) of triethylamine, the solution is cooled and 6.3 g (68 mmol) of propinyl chloride is added without exceeding 5° C.

The suspension is stirred for 2 hours 30 minutes at ambient temperature then extracted successively by 400 ml of 5% ammonia solution, 400 ml of 5% HCl solution then by water until it is neutralised.

The methylene chloride is evaporated and the oily residue (18.8 g) is purified by chromatography (compound II.2 of formula II.2.2 R1=R5=C6H5; R2=C2H5; R3=CH3; R7=C2H5; Q=—CH=CH—)

| Weight: 16.2 g | Rdt = 89% | CCM: 0.40; S.G. |

RMN: 0.75 (t,3H); 1.05 (t,3H); 1.75–2.50 (m,4H); 2.80–3.60 (m,5H); 5.75–6.50 (m,2H); 7.10–7.50 (m,10H)

b) 6.7 g (50 mmol) of aluminum chloride is introduced in a reactor protected from humidity at −7° C. then 85 ml of diethyl ether is added quickly. The solution obtained is continuously stirred. Simultaneously, 5.7 g (150 mmol) of aluminum lithium hydride is introduced into another reactor protected from humidity then 85 ml of anhydrous THF at −70° C. The suspension is continuously stirred for 20 minutes at 8° C. then introduced into the etherised ammonium chloride solution.

A solution of 16.0 g (50 mmol) of carboxamide prepared in a) in 40 ml of THF is added at a temperature below 25° C. The mixture is kept at ambient temperature for 1 hour then cooled to 0 C. The complexes are decomposed by the addition of a 10% NaOH solution then adding water.

The insoluble substance is filtered and the filtrate evaporated in a vacuum and and in a boiler. The pale yellow oily residue (13 g) is purified by chromatography.

| Weight = 12.0 g | Rdt = 78% | CCM: 0.80; S.H. |

RMN: 0.60–0.95 (q,6H); 1.20–1.60 (m,2H); 1.70–2.05 (q,2H); 2.15–2.60 (m,5H); 2.85 (d,2H); 6.00–6.55 (m,10H)

Example 48

ã-(3.4 dichloro)cinnamyl-N,N-dimethyl-ã-methyl-benzylamine (I.3; R1=C6H5; R2=R3=R4 —CH3; R5=3,4Cl2-C6H3; Q=—CH=CH—)

8.9 g (29 mmol) of ã-(3,4 dichloro)cinnamyl-ã-methyl-benzylamine (example 9) is mixed with 5.1 ml (68 mmol) of aqueous formaldehyde solution at 37% (w/v - d=1.083) in a balloon flask while stirring and at ambient temperature.

The heterogeneous mixture is stirred for 30 minutes at the laboratory temperature then approximately 3.3 ml (87.5 mmol) of pure formic acid (d=1.22) is added drop by drop in approximately 5 minutes. A solution is obtained which is heated while stirring in the heated boiler for 1 hour.

The solution is cooled, 50 ml of 2N HCl solution is added then extracted by 3×60 ml of ether. The acidic aqueous phase is alkalined in a cold condition up to PH 12 then extracted by 3 times 100 ml of ether.

The etherised phases washed with water then dried on MgSO4 are distilled in a boiler. The residue is purified by chromatography.

| Weight: 4.3 g | Rdt = 44% | CCM: 0.45-0.55; S.M. |
|---|---|---|

RMN: 1.35 (s,3H); 2.20 (s,6H); 2.60 (m;2H); 5.70-6.30 (m,2H); 6.80-7.70 (m,8H) Chlorohydrate:

| Rdt = 87% | F = 174° C. (methanol-ether) |
|---|---|

Anal. (C19H21C12N.HC1) C,H,Cl,N

Example 49

(−)ā-cinnamyl-N,N-dimethyl-ā-ethylbenzylamine (I.3; R1=R5=C6H5; R2=C2H5; R3=R4=CH3; Q=—CH=CH—)

18.3 g (0.073 mol) of (+) ā-cinnamyl-ā-ethyl-benzylamine obtained as in example 16A and 91.0 ml of formaldehyde solution at 37% (w/v) (1.12 mol) is introduced into 365 ml of acetonitrile in a reactor in a nitrogen atmosphere.

13.65 g (0.217 mol) of sodium cyanoborohydride is added at 0° C. while stirring. Two colourless phases are formed, to which are then added 13.53 ml (0.230 mol) of pure acetic acid in 10 minutes approximately and at 10° C. The mixture is stirred for one hour at approximately 30° C., then at 20° C.18 ml of formaldehyde solution at 37% (w/v) (0.0220 mol) then 4.50 g of sodium cyanoborohydride (0.072 mol) and 4.55 ml of pure acetic acid are added.

The same quantities of the same reagents are then added again after stirring for 1 hour at ambient temperature then stirred for 2 hours 30 minutes at ambient temperature then 700 ml of ether added and the aqueous phase decanted which is separated.

The organic phase is washed by successive extractions with 200 ml of N sodium hydroxide solution then with water and finally with a saturated sodium chloride solution. A residue of 21.0 g is obtained after dehydration and evaporation of the ether, which is purified by crystallisation in 60 ml of ethanol at 95%.

The insoluble substance is filtered and dried in a vacuum at ambient temperature.

| Weight: 16.6 g | F = 48° C. | Rdt = 81.4% |
|---|---|---|

CCM: 0.40-0.50; S.M.
[ā]$_D^{25}$= −21.6° C. (c=6.0%; MeOH)
RMN: 0.80 (t,3H); 1.90 (q,2H); 2.25 (s,6H); 2.90 (d,2H); 6.009-6.60 (m,2H); 7.10-7.55 (m,10H).
Chlorohydrate:
Prepared in the conventional manner, starting from 16.6 g (0.059 mol) of the previous product and some 44.0 ml of hydrochloric ether solution of approximately 4N, the coarse product obtained after evaporating the solvent is purified by recrystallisation in 90 ml of ethyl acetate. The precipitate is filtered and dried in a vacuum.

| Weight: 14.4 g | F = 167° C. | Rdt = 77.2% |
|---|---|---|

Anal. (C20H25N,HCl) C,H,Cl,N
[ā]$_D^{25}$= +26.7° (c=2.10; H2O)

Example 50

(+) ā-cinnamyl-N,N-dimethyl-ā-ethyl-benzylamine (I.3; R1=R5=C6H5; R2=C2H5; R3=R4=CH3; Q=—CH=CH—)

Proceeding as has been indicated in example 49 above and starting from 18.3 g (0.073 mol) of (−)ā-cinnamyl-ā-ethyl-benzylamine prepared as in example 16B the product is obtained and purified by crystallisation in ethanol at 95%.

| Weight: 12.8 g | F = 48° C. | Rdt = 77.2% |
|---|---|---|

CCM: 0.40-0.50; S.L.
[ā]$_D^{25}$= +20.8° (c=5.8%; MeOH)
RMN: 0.80 (t,3H); 1.90 (q,2H); 2.25 (s,6H); 2.90 (d,2H); 6.00-6.60 (m,2H); 7.10-7.55 (m,10H)
Chlorohydrate:
Obtained as described in example 49 above and starting from 12.8 g (0.046 of product and 34 ml of approximately 4N hydrochloric ether, the product is purified by recrystallisation in 60 ml of ethyl acetate.

| Weight: 1.4 g | F = 167° C. | Rdt = 78.5% |
|---|---|---|

Anal. (C20H25N,HCl) C,H,Cl,N
[a]$_D^{25}$=25.8° (c=2.15%; H2O)

Example 51

(−)
ā-cinnamyl-N,N-dimethyl-ā-ethyl-p.chlorobenzylamine (I.3; R1=p.Cl-C6H4; R2=C2H5; R3=R4 CHJ3; R5=C6H5; Q=—CH=CH—)

The compound is prepared starting from the (+) ā-cinnamyl ā-ethyl-p.chlorobenzylamine of the example in 17 A and using the method of operation described in example 49.

| Rdt = 68% | F = 62° C. (ethanol) | CCM: 0.70; S.L. |
|---|---|---|

[ā]$_d^{20}$= −23.7° (c=2.60%; MeOH)
RMN: 0.75 (t,3H); 1.85 (q,2H); 2.25 (s,6H); 2.80 (d,2H); 5.95-6.55 (m,2H); 7.10-7.45 (m,9H)

Example 52

(+)
ā-cinnamyl-N,N-dimethyl-ā-ethyl-p.chlorobenzylamine (I.3; R1=p.Cl-C6H4; R2=C2H5; R3=R4=CH3; R5=C6H5; Q=—CH=CH)

Starting from (−) ā-cinnamyl-ā-ethyl-p. chlorobenzylamine of example 17 B and in accordance with the method of operation of example 49.

| Rdt = 59% | F = 62° C. (ethanol) | CCM: 0.70; S.L. |

$[\tilde{a}]_D^{20} = +24.2°$ (c=2.55%; MeOH)

RMN: 0.75 (t,3H); 1.85 (q,2H); 2.25 (s,6H); 2.80 (d,2H); 5.95–6.55 (m,2H); 7.10–7.45 (m,9H).

Prepare the compounds of the invention (I.3) of examples 53 to 70 below reaction of the various derivatives of amino acetonitriles described in example 2 with ethylmagnesium bromide as described in example 2 according to the experimental protocol.

Example 53: trans N,N-dimethyl-ã-ethyl-ã-(2-phenyl-1-cyclopropylmethyl)-benzylamine
(R1 = R5 = C6H5; R2 = C2H5; R3 = R4 = CH3; Q = cyclopropylene 1,2 diyl)
Starting from the compound in example 2.aa
Rdt = 47% Eb/0.1 - 142–152° C. CCM: 0.60; S.C.
RMN: 0.65–2.15 (m,11H); 2.26 (d,6H); 6.87–7.50 (m,10H)
Anal. (C21H27N) C,H,N Example 54: trans N,N-dimethyl-ã-ethyl-ã-(2-phenyl-1-cyclopropylmethyl)-3,4,5-trimethoxybenzylamine
(R1 = 3,4,5(CH3O)3-C6H2; R2 = C2H5; R3 = R4 = CH3; R5 = C6H5; Q = cyclopropylene 1,2 diyl)
Starting from the compound of example 2.h
Rdt = 38% CCM: 0.35; S.C.
RMN: 0.62–0.95 (m,6H); 1.41–1.61 (m,1H); 1.87–2.02 (m,4H); 2.31 (d,6H); 3.70–3.88 (t,9H); 6.66 (s,2H); 6.90–7.22 (m,5H)
Anal. (C24H33NO3) C,H,N,O Example 55: N,N-dimethyl-ã-ethyl-ã-[3O(2-thienyl)-2-propenyl]-benzylamine
Starting from the compound of example 2.i
Rdt = 62% F = 77–78° C. CCM: 0.60–0.65; S.C.
RMN: 0.72 (t,3H); 1.90 (q,2H); 2.25 (s,6H); 2.80 (d,2H); 5.90–6.22 (dt,1H); 6.58 (d,1H); 6.89–7.41 (m,8H)
Anal. (C18H23NS) C,H,N,S Example 56: N,N-dimethyl-ã-ethyl-ã-[3O(3-thienyl)-2-propenyl]-benzylamine
(R1 = C6H5; R2 = C2H5; R3 = R4 = CH3; R5 = 3-thienyl; Q = —CH=CH—)
Starting from the compound of example 2.j
Rdt = 58% F = 95–96° C. CCM: 0.50
RMN: 0.78 (t,3H); 1.95 (q,2H); 2.26 (s,6H); 2.87 (d,2H); 5.90–6.26 (dt,1H); 6.55 (d,1H); 7.05–7.50 (m,8H)
Anal. (C18H23NS) C,H,N,S Example 57: trans N,N-dimethyl-ã-ethyl-ã-[2O(3,4,5O-trimethoxyphenyl)-1-cyclopropylmethyl]-benzylamine
(R1 = C6H5; R2 = C2H5; R3 = R4 = CH3; R5 = 3,4,5(CH3O)3-C6H2; Q = cyclopropylene 1,2 diyl)
Starting from the compound of example 2.ma
Rdt = 37% CCHM: 0.45; S.M.
RMN: 0.95–1.15 (m,6H); 1.88 (m,2H); 2.48 (m,1H); 2.71 (s,6H); 3.30 (m,2H); 3.77 (d,9H); 6.33 (s,2H) 7.50–7.82 (m,5H)
- Chlorohydrate: F = 205–208° C.
Anal. (C24H3NO3.HCl) C,H,N,O,Cl Example 58: trans N,N-dimethyl-ã-ethyl-ã-(2-phenyl-1-cyclopropylmethyl)-(2-pyridyl)methanamine
(R1 = 2-pyridyl; R2 = C2H5; R3 = R4 = CH3; R5 = C6H5; Q = cyclopropylene 1,2 diyl)
Starting from the compound of example 2.t
Rdt = 52% Eb/0.1 = 130° C. CCM: 0.30; S.E.>
RMN: 0.66–0.91 (m,5H); 1.44–1.63 (m,2H); 1.80–2.24 (m,4H); 2.30 (s,6H); 6.89–7.35 (m,6H); 7.52–7.69 (m,2H) 8.62 (d,1H)
Anal. (C20H26N2) C,H,N Example 59: ã-cinnamyl-N,N-dimethyl-ã-ethyl-2-furfurylamine
(R1 = 2-furyl; R2 = C2H5; R3 = R4 = CH3; R5 = C6H5; Q = —CH=CH—)
Starting from the compound of example 2.u
Rdt = 37% CCM: 0.35; S.>C.
RMN: 1.81 (t,3H); 1.86 (q,2H); 2.20 (s,6H); 2.62–2.85 (m,2H); 5.98–6.58 (m,4H); 7.21–7.38 (m,6H)
Anal. (C18H23NO) C,H,N,O Example 60: trans N,N-dimethyl-ã-ethyl-ã-(2-phenyl-1-cyclopropylmethyl)-2-furfurylamine
(R1 = 2-furyl; R2 = C2H5; R3 = R4 = CH3; R5 = C6H5; Q = cyclopropylene 1,2 diyl)
Starting from the compound of example 2.ua
Rdt = 65% CCM: 0.40; S.A.
RMN: 0.80–0.97 (m,6H); 1.23–1.70 (m,1H); 1.91–2.03 (m,4H); 2.16 (s,6H); 6.06 (d,1H); 6.26 (dd,1H); 6.80–7.20 (m,5H); 7.32 (d,1H)
Anal. (C19H26NO) C,H,N,O Example 61: N,N-dimethyl-ã-ethyl-ã-[3-(2-thienyl)-2-propenyl]-2-furfurylamine
(R1 = 2-furyl; R2 = C2H5; R3 = R4 = CH3; R5 = 2-thienyl; Q = —CH=CH—)
Starting from the compound of example 2.ub
Rdt = 56% F = 68–69° C. CCM: 0.50–0.55; S.C.
RMN: 0.85 (t,3H); 1.90 (q,2H); 2.25 (s,6H); 2.80 (m,2H); 5.80–6.12 (dt,1H); 6.18 (m,1H); 6.34 (m,1H); 6.60 (d,1H); 6.90–7.12 (m,3H); 7.40 (d,1H)
Anal. (C16H21NOS) C,H,N,O,S Example 62: ã-cinnamyl-N,N-dimethyl-ã-ethyl-2-thienylmethylamine -continued (R1 = 2-thienyl; R2 = C2H5; R3 = R4 = CH3; R5 = C6H5; Q = —CH=CH—)
Starting from the compound of example 2.v
Rdt = 32% CCM: 0.45-0.50; S.C.
RMN: 1.87 (t,3H); 1.94 (q,2H); 2.24 (s,6H); 2.86 (d,2H); 6.05-6.63 (ddt,2H);
6.87-7.07 (m,2H); 7.17-7.37 (m,6H)
Anal. (C18H23NS) C,H,N,S Example 63: trans N,N-dimethyl-ā-ethyl-ā-(2-phenyl-1-cyclopropylmethyl)-2-thienylmethylmaine (R1 = 2-thienyl; R2 = C2H5; R3 = R4 = CH3; R5 = C6H5; Q = cyclopropylene 1,2 diyl)
Starting from the compound of example 2.va
Rdt = 58% Eb/0.1 = 155-167° C. CCM: 0.60; S.C.
RMN: 0.75-0.98 (m,6H); 1.55-1.77 (m,1H0; 2.00-2.10 (m,4H); 2.23 (s,6H); 6.83-7.26 (m,8H)
Anal. (C19H26NS) C,H,N,S Example 64: N,N-dimethyl-ā-ethyl-ā-[3-(2-furyl)-2-propenyl]-2-thienylmethylamine (R1 = 2-thienyl; R2 = C2H5; R3 = R4 = CH3; R5 = 2-furyl; Q = —CH=CH—)
Starting from the compound of example 2.vb
Rdt = 515 F = 59-60° C. CCM: 0.50-0.55; S.C.
RMN: 0.85 (t,3H); 1.95 (q,2H); 2.25 (s,6H); 2.85 (m,2H); 6.10-6.35 (m,4H0; 6.85-7.06 (m,2H0; 7.23-7.32 (m,2H)
Anal. (C16H21NOS) C,H,N,O,S Example 65: N,N-dimethyl-ā-ethyl-ā-[3-(2-thienyl)-2-propenyl]-2-thienylmethylamine (R1 = 2-thienyl; R2 = C2H5; R3 = R4 = CH3; R5 = 2-thienyl; Q = —CH=CH—)
Starting from the compound of example 2.vc
Rdt = 65% F = 69-71° C. CCM: 0.60; S.C.
RMN: 0.72 (t,3H); 1.90 (q,2H); 2.25 (s,6H); 2.80 (d,2H); 6.08 (dt,1H); 6.60
(d,1H); 6.82-7.25 (m,6H).
Anal. (C16H21NS2) C,H,N,S Example 66: N,N-dimethyl-ā-ethyl-ā-[3-(3-thienyl)-2-propenyl]-2-thienylmethylamine (R1 = 2-thienyl; R2 = C2H5; R3 = R4 = CH3; R5 = 3-thienyl; Q = —CH=CH—)
Starting from the compound of example 2.vd
Rdt = 61% F = 85.5-86° C. CCM: 0.40; S.M.
RMN: 0.90 (t,3H); 1.95 (q,2H); 2.25 (s,6H); 2.85 (d,2H); 5.90-6.25 (m,1H); 6.60
(d,1H0; 6.90-7.35 (m,6H)
Anal. (C16H21NS2) C,H,N,S Example 67: ā-cinnamyl-N,N-dimethyl-ā-ethyl-3-thienylmethylamine (R1 = 3-thienyl; R2 = C2H5; R3 = R4 = CH3; R5 = C6H5; Q = —CH=CH—)
Starting from the compound of example 2.w
Rdt = 45% F = 91° C. CCM: 0.60-0.65; S.E.
RMN: 0.83 (t,3H); 1.92 (q,2H); 2.20 (s,6H); 2.75-3.00 (d,2H); 6.00-6.65 (m,2H);
6.90-7.45 (m,8H).
Anal. (C18H23NS) C,H,N,S Example 68: trans N,N-dimethyl-ā-ethyl-ā-(2-phenyl-1-cyclopropylmethyl)-3-trienylmethylamine (R1 = 3-thienyl; R2 = C2H5; R3 = R4 = CH3; R5 = C6H5; Q = cyclopropylene 1,2 diyl)
Starting from the compound of example 2.wa
Rdt = 47% Eb/0.05-140° C. CCM: 0.30; S.B.
RMN: 0.85-1.05 (m,6H); 1.55-2.10 (m,5H0; 2.25 (s,6H0; 6.90-7.50 (m,8H)
Anal. (C19H26NS) C,H,N,S Example 69: N,N-dimethyl-ā-ethyl-ā-[3-(2-thienyl)-2-propenyl]-3-thienylmethylamine (R1 = 3-thienyl; R2 = C2H5; R3 = R4 = CH3; R5 = 2-thienyl; Q = —CH=CH—)
Starting from the compound of example 2.wb
Rdt = 64% F = 91-92° C. CCM: 0.50; S.E.
RMN: 0.85 (t,3H); 1.95 (q,2H); 2.2 (s,6H); 2.8 (d,2H); 5.9-6.25 (m,1H); 6.65
(d,1H); 6.9-7.35 (m,6H)
Anal. (C16H21NS2) C,H,N,S Example 70: N,N-dimethyl-ā-ethyl-ā-[3-(3-thienyl)-2-propenyl]-3-thienylmethylamine (R1 = 3-thienyl; R2 = C2ZH5; R3 = R4 = CH3; R5 = 3-thienyl; Q = —CH=CH—)
Starting from the compound of example 2.wc
Rdt = 59% F = 104-105° C. CCM: 0.40; S.E.
RMN: 0.85 (t,3H); 1.95 (q,2H); 2.2 (s,6H); 2.85 (d,2H); 5.9-6.6 (m,2H); 7.05-7.40 (m,6H)
Anal. (C16H21NS2) C,H,N,S The toxicological and pharmacological tests carried out on the ethylamines of the invention of formula (I) described in examples 3 to 70 above demonstrate their low toxicity as well as important psychotropic properties which make these compounds useful for treating neurophysical complaints. In addition, certain tests demonstrate the group of compounds of formula (I.A) and defined by special meanings referred to previously for R1, R3/R4 and R5, an "in vitro" bonding activity with opiated receptors and more particularly with the mu receptors. This affinity is translated "in vivo" by an activity on the urinary tract, which consists of an action on the vesicular parameters of the rat.

The study of the toxicity of the products of the invention is researched on mice by oral channel by the approximate determination of their DL 50 which is the lethal dose causing 50% of deaths in the animals in the conditions of the experiment. It is carried out on batches of four male "Swiss" mice weighing approximately 20 g with an empty stomach from the day before the test. Each determination is carried out with four doses of products corresponding respectively to an administration of 100, 300, 600 and 1000 mg of product, expressed in the basic form per kg of animal.

It has also been observed that the products of the invention generally have an acute toxicity of DL50 greater than or equal to 1000 mg/kg. Exceptionally certain compounds have a DL50 of approximately 600 mg/kg.

The psychotropic properties of the compounds have been determined by the protection of the induced convulsion by picrotoxine for mice, which is achieved by the method derived from that of Krall et al., "Epilepsia", 1978, 19, p. 409–428.

The administration of picrotoxine caused a convulsive crisis in the animal characterised by a myoclonic extension syndrome followed by the extension of the limbs causing the animal to die. Certain substances, particularly those active on the complex GABA/benzodiazepines/Cl-ionophore makes it possible to protect the animals from this convulsive crisis.

In practice the study is carried out on batches of 10 male "Swiss" mice weighing approximately 20 g, which are administered with the product to be studied in aqueous solution either by intraperitoneal route (i.p.) at the rate of 50 mg/kg and in a volume of 0.2 ml of solution per animal, or by oral route (p.o) in a volume of 2.0 ml of solution per animal.

An injection of a solution of picrotoxine at the rate of 24 mg/kg in a volume of 0.2 ml per animal is then administered by interperitoneal route, either 30 minutes after administering the product by interperitoneal route or 60 minutes after administering the product by oral route. The dose of the product injected causing a clonic crisis, which results in untreated animals dying. The suppression of the extension tonic phase in the animals treated under the conditions of the test is observed. The results are expressed:

either in percentages of protected animals of this phase to the reaction of 50 mg/kg of the compound of the study administered by i.p. route or 100 mg/kg by p.o route, or in DE50 for each of these routes, which is the efficient dosage of the test compound expressed in mg/kg protecting 50% of the animals of this extension phase. The significant value of the results being generally indicated in the following manner:

* Significant result at $p<0.05$
** Significant result at $p<0.01$
*** Significant highly significant at $p<0.001$.

The results of the study have been recorded for the products of the inventions of formulae (I.1), (I.2) and (I.3) in tables 1,2, 3 (1) and 3(2) below:

TABLE 1

| | Results - Compound I.1 | |
|---|---|---|
| Example | i.p.: % prot. or DE50 | p.o.: % prot. or DE50 |
| 3 | 80%*** | 100%*** |
| 4 | 60%* | N.T. |
| 5 | 50%* | N.T. |
| 6 | 70%** | 70%*** |
| 7 | 100%*** | N.T. |
| 8 | 80%*** | N.T. |
| 9 | 100%*** | N.T. |

TABLE 1-continued

| | Results - Compound I.1 | |
|---|---|---|
| Example | i.p.: % prot. or DE50 | p.o.: % prot. or DE50 |
| 10 | 90%*** | N.T. |
| 11 | 70%** | 100%*** |
| 12 | DE50 = 37,3 | DE50 = 50,0 |
| 13 | DE50 = 23,2 | 50%*** |
| 15 | DE50 > 25,0 | N.T. |
| 16A | 90%*** | 100%*** |
| 16B | 100%*** | 100%*** |
| 17A | 80%*** | 50%* |
| 17B | 80%*** | 50%* |

N.T. Not tested

TABLE 2

| | Results - Compounds I.2 | |
|---|---|---|
| Example | i.p.: % prot. or DE50 | p.o.: % prot. or DE50 |
| 18 | 80%*** | 100%*** |
| 19 | 70%** | N.T. |
| 20 | N.T. | 80%*** |
| 21 | 90%*** | 70%** |
| 22 | 80%*** | 100%*** |
| 23 | 60%* | 100%*** |
| 24 | N.T. | DE50 = 73,5% |
| 25 | N.T. | 50%* |
| 28 | 100%*** | 100%*** |
| 29 | 100%*** | 100%*** |

N.T. Not tested

TABLE 3(1)

| | Results - Compounds I.3 | |
|---|---|---|
| Example | i.p.: % prot. or DE50 | p.o.: % prot. or DE50 |
| 30 | 100%*** | 100%*** |
| 31 | 100%*** | 50%* |
| 32 | 50%* | 60%* |
| 34 | 80%*** | 60%* |
| 35 | 90%*** | DE50 = 40,3 |
| 36 | N.T. | 100%*** |
| 38 | 80%*** | N.T. |
| 40 | DE50 = 16,6 | DE50 = 37,7 |
| 41 | N.T. | DE50 = 78,4 |
| 42 | N.T. | DE50 = 65,0 |
| 44 | DE50 = 21,4 | DE50 = 23,9 |
| 46 | DE50 = 29,8 | DE50 = 35,4 |
| 47 | DE50 = 58,2 | DE50 = 65,0 |
| 48 | 90%*** | N.T. |
| 49 | 100%*** | 100%*** |
| 50 | 100%** | 100%*** |

N.T. Not tested

TABLE 3(2)

| | Results - Compounds I.3 | |
|---|---|---|
| Example | i.p.: % prot. or DE50 | p.o.: % prot. or DE50 |
| 52 | 70%** | 90%*** |
| 54 | 70%** | N.T. |
| 55 | 70%** | 70%** |
| 56 | 70%** | 80%** |
| 58 | 70%** | 80%*** |
| 59 | 90%*** | 100%*** |
| 60 | 80%*** | 60%* |
| 61 | 50%*** | N.T. |
| 62 | N.T. | 80%** |
| 63 | 60%* | 50%* |
| 64 | 70%* | 50%* |
| 65 | 90%*** | 50%* |
| 67 | 70%* | 100%*** |
| 68 | 100%*** | N.T. |
| 69 | 90%*** | 80%** |

TABLE 3(2)-continued

| | Results - Compounds I.3 | |
|---|---|---|
| Example | i.p.: % prot. or DE50 | p.o.: % prot. or DE50 |
| 70 | 80%*** | 100%*** |

N.T. Not tested

These results demonstrate an activity in the test on the products of the invention investigated for protection against convulsions induced in mice by picrotoxines and independently of the method of administration used.

Among other things and as has been stated previously, the group of compounds (IA) which are active "in vitro" on opiated receptors.

The analysis is carried out in accordance with the technique described by F. Roman et al. in J. Pharm. Pharmcol. 1987, 39, p. 404-407 which consists of analysing the displacement of specific radioactive ligands of the opiated mu, delta and kappa sub receptors by the action of the test products on the membranous receptors of a guinea pig.

The results of the investigation are listed in Table 4 and are expressed in CI50 which are the nanomolar concentrations of the products in solution capable of inhibiting 50% of the specific radioactive ligand bonds with the receptor considered. Morphine was used by virtue of the reference product.

TABLE 4

Bonding affinity of the compounds (IA) of the invention to the mu, delta and kappa receptors

| | CI50 affinity | | |
|---|---|---|---|
| Example | mu rec. | delta rec. | kappa rec. |
| 17B | 11,4 | N.T. | N.T. |
| 19 | 200 | 3490 | 264 |
| 23 | 80 | 1380 | 340 |
| 24 | 21 | 1405 | 410 |
| 25 | 56 | 1591 | 875 |
| 26 | 28 | 1072 | 458 |
| 31 | 80 | 1340 | 210 |
| 33 | 50 | 1230 | 120 |
| 35 | 60 | 1280 | 290 |
| 36 | 90 | 680 | 220 |
| 37 | 100 | 150 | 230 |
| 43 | 16 | 434 | 197 |
| 44 | 4 | 223 | 110 |
| 46 | 12 | 260 | 235 |
| 52 | 7 | N.T. | 99 |
| Morphine | 7 | 152 | 127 |

Although generally less than those shown by morphine, the affinity of the compounds with the receptors are nevertheless significant. They attain the same order of intensity as the reference products for the compounds in examples 43, 44 and 46.

Also in a general sense the compounds have a preferential but non-specific affinity for the mu receptors. To a lesser degree they are also active on the kappa receptors and much less on the delta receptors.

The activity of the opiated compounds "in vivo" on the urinary tract has been described by various authors. C. Soulard et al. in "Advanced in the Biosciences" Vol. 75, 1989, show that the compounds with mu affinity and the compounds with kappa affinity have different activities on the bladder of the rat.

Hence the mu compounds will inhibit the vesical motivity, the kappa compounds will activate it, and it has also been shown that the mu-kappa compounds of mixed affinity have an inhibiting activity of this motivity.

Studies by a similar method of operation, the compounds of the invention (I.A) which show a mu and kappa affinity also have an activity on certain functional parameters of the bladder of the rat which justifies their interest in the treatment of dysfunctions in the urinary tract.

The study carried out consists of transvesical cystomanometry on a wide awake rat. The following was measured during the storage and emission phases of urine under continuous intervesical perfusion of sterile physiological serum:

the "threshold pressure", which is the intervesical pressure immediately preceding the contraction phase of the detrusor the volume of each urinary emission.

The technique used in the female rat consisted of preparing the animals 48 hours before the actual experiment by effecting the implantation of two catheters in the apex of the bladder and one catheter in the left-hand jugular vein under anaesthetic, with the external end of these catheters being protected and held by a sticking plaster corset.

The animals were placed in suitable cages at the time of the test, which were equipped so as to collect and measure the urine. For each animal one vesical catheter was connected to a pressure sensor, the other to a perfusor which supplied 0.2 ml/min. of sterile physiological serum continuously.

The intravesical pressure was measured continuously during the perfusion and it was possible to observe:

a filling phase of the bladder during which the pressure increased progressively, a sudden rising phase of this pressure during the contraction of the detrusor: the "threshold" pressure which is the pressure observed just before the pressure of the contraction phase. This threshold pressure was raised in the same way as the urinary volume at each urination.

The study consisted of observing the changes in these parameters by the action of the products (IA) which were administered in solution by intravenous route by means of the catheter placed in the left jugular vein.

Dicyclomine and Baclofen which have been considered for the treatment of hyperactive bladders (Drugs of Today, Vol. 24, no. 5, 1988, p. 337-348) were also used in this test in the form of comparison products.

TABLE 5

| | Urological activity | | |
|---|---|---|---|
| Example | Dose i.v. mg/kg | % variation pressure threshold | % variation volume |
| 19 | 5,0 | +354 | +54 |
| 23 | 5,0 | +196 | +35 |
| 25 | 5,0 | −85 | +67 |
| 26 | 5,0 | +229 | +93 |
| 31 | 0,5 | +73 | +44 |
| 33 | 0,5 | +199 | +27 |
| 35 | 1,0 | +200 | −39 |
| 36 | 1,0 | +125 | +36 |
| 37 | 5,0 | +188 | −53 |
| 43 | 1,0 | +109 | −91 |
| 44 | 0,5 | +183 | −56 |
| 46 | 1,0 | −111 | −44 |
| 52 | 0,5 | +72 | −30 |
| Dicyclomine | 2,5 | +28 | −20 |
| Baclofen | 2,5 | +113 | −32 |

These results prove the activity of these compounds of the invention on the urinary tract of an animal. More particularly the important activity of the compounds of examples 31, 33, 35, 36, 43, 44, 46 and 52 of the invention compared to that of the reference compounds is also noted.

Hence in relation to Baclofen, which is the most active comparative product in these tests and taking into consideration the dosage of the compounds effectively administered, the compounds of examples 33 and 44 have an activity of 5 to 10 times above the threshold pressure whereas the examples 43 and 44 appeared to be 5 to 10 times more active for the variation in volume.

Consequently, pharmacological studies which have just described all the (I) compounds are useful for treating neuro=psychical diseases and may allow the treatment of patients with humour and/or behaviour disorders in the form of medicines.

More particularly, the compounds (IA) defined previously have "in vitro" bonding affinity with opiated receptors and particularly with mu and kappa receptors, which appear to correspond with an observable activity on the urinary tract at the bladder level. These products are suitable for therapy for dysfunction of unstable bladders and in the form of medicine that can be used to treat disorders in urination and incontinence.

Presented in pharmaceutical form, the conventional effective unitary doses are between 1 and 500 mg and more particularly between 5 and 200 mg of product depending on the age and gravity of the disorder to be treated. The daily therapeutic doses may be divided into several smaller doses of between 5 and 2000 mg of product per day. In a general way a daily posology of 50 to 500 mg of product divided into 2 to 4 smaller doses is satisfactory.

The products of the invention are administered to the patients to be treated in the form of medicines adapted to the disorder to be treated. Depending on the cases, the medical preparations shall be in the form of tablets, sugar coated pills, capsules, powders, solutions, suspensions, gels or suppositories, as nonexhaustive examples. These pharmaceutical forms are prepared from products in the basic form or of their salts and by the methods currently used in this industry.

Generally, the active element in the forms of solid medicines represents 5 to 90% by weight of the total of the final version whereas the vehicles represent 95 to 10%. In the liquid forms, which can be considered as those where the proportion of active element is between 0.1 and 10% by weight of the final form whereas the vehicles may represent 99.9 to 90% of the weight of this form.

The formulation and preparation of injectable isotonic solutes, those in the form of tablets and those in the form of gels administered orally have been shown below in the form of examples.

Injectable isotonic solution

Formula:

| | |
|---|---|
| Active substance of example 9 (chlorohydrate) | 10 mg |
| Sodium chloride | 9 mg |
| Distilled water in sufficient quantity | 1.0 ml |

Preparation:
The isotonic solution is divided into suitable volume phials, which are sterilised by conventional known thermal methods after sealing or in fact the solution is sterilised by filtration, divided into phials which are then sealed, with the whole operation carried out in a sterile atmosphere.

In the latter case it is preferred to add 1% of benzyl alcohol as bacteriostatic agent to the formula described, i.e. 10 mg of this alcohol per ml of solute.

Pills

Formula:

| | |
|---|---|
| Active substance of example 31 | 10.0 to 50.0 mg |
| Polyvinylpyrrolidone | 20.0 mg |
| Carboxymethylstarch | 8.0 mg Magnesium |
| stereate | 2.0 mg |
| Colloidal silicon | 0.4 mg |
| Lactose in sufficient quantity for | 200.0 mg |

Preparation:
The active element is mixed with the lactose then granulated with the polyvinylpyrrolidone in solution. The grains are dried and sifted on a grille with 1mm mesh. The carboxymethylamidon is mixed with the colloidal silicon then added to the granulates. It is then intimately mixed with the magnesium stereate then compressed in the form of 200.0 mg per pill.

Gel

Formula:

| | |
|---|---|
| Active substance of example 30 (chlorohydrate) | 0.20 to 0.60 g |
| Hydroxypropylcellulose | 2.00 g |
| Sodium saccharinate | 0.01 g |
| Sorbitol syrup at 70% (w/v) | 25.00 g |
| Natural strawberry aroma | 0.50 g |
| Preservative | 0.10 g |
| Purified water in quantity sufficient for | 100.00 g |

Preparation:
The preservatives and the sodium saccharinate are dissolved in water, then while stirring, add the hydroxypropylcellulose while dispersing. Continue stirring until a gel is obtained with sorbitol syrup added while still stirring, then finally the aroma.

We claim:

1. Substituted ethylamines of the formula

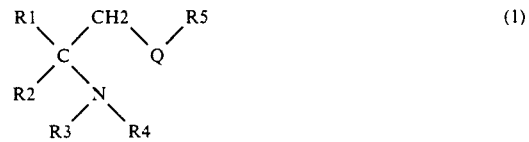

in which:
R1 is phenyl possibly mono, di or trisubstituted by halogen atoms, by lower alkyl, lower haloalkyl or lower alkoxy radicals,
R2 is lower alkyl
R3 and R4, identical or different, are hydrogen, lower alkyl or lower alkenyl radicals
R5 is phenyl, possibly mono, di or trisubstituted by halogen atoms or by lower alkoxy radicals,
Q represents a —CH=CH— group, their addition salts with acids and their optically active forms.

2. Ethylamines as in claim 1, in which R1 is phenyl.

3. Ethylamines as in claims 1 or 2 in which R5 is phenyl.

4. Ethylamines as in one of the claims 1 to 3 inclusive, in which R2 is ethyl.

5. Ethylamines as in one of the claims 1 to 4 in which R3 is hydrogen or methyl and R4 is hydrogen or methyl.

6. Ethylamines as in claim 1, in which at one and the same time R1 and R5 are phenyl, one of the two at least being substituted, R3 and R4 identical or different are hydrogen or lower alkyl, nevertheless without being hydrogen.

* * * * *